United States Patent [19]
Marburg et al.

[11] Patent Number: 5,623,057
[45] Date of Patent: Apr. 22, 1997

[54] PNEUMOCOCCAL POLYSACCHARIDE CONJUGATE VACCINE

[75] Inventors: Stephen Marburg, Metuchen; Richard L. Tolman, Warren, both of N.J.; Peter J. Kniskern, Lansdale, Pa.; William J. Miller, North Wales, Pa.; Arpi Hagopian, Lansdale, Pa.; Charlotte C. Ip, Blue Bell, Pa.; John P. Hennessey, Jr., Dublin, Pa.; Dennis J. Kubek, Salem, W. Va.; Pamela D. Burke, Lansdale, Pa.

[73] Assignee: Merck & Co., Inc., Rahway, N.J.

[21] Appl. No.: 246,394

[22] Filed: May 20, 1994

Related U.S. Application Data

[63] Continuation of Ser. No. 807,942, Dec. 19, 1991, abandoned, which is a continuation-in-part of Ser. No. 646,570, Jan. 28, 1991, abandoned.

[51] Int. Cl.$^6$ .......................... C07K 17/02; A61K 39/385
[52] U.S. Cl. .......................... 530/404; 530/403; 530/405; 530/406; 530/408; 530/409; 530/410; 530/411; 424/193.1; 424/194.1; 424/197.11; 424/234.1; 424/237.1; 424/241.1; 424/244.1; 424/256.1; 424/260.1
[58] Field of Search ................................ 530/403–406, 530/408–411; 424/194.1, 193.1, 197.11, 234.1, 261.1, 237.1, 244.1, 256.1, 260.1

[56] References Cited

U.S. PATENT DOCUMENTS

| | | | |
|---|---|---|---|
| 4,221,906 | 9/1980 | Querry et al. | 536/1.1 |
| 4,242,501 | 12/1980 | Cano et al. | 536/1.1 |
| 4,271,147 | 6/1981 | Helting et al. | |
| 4,459,286 | 7/1984 | Hilleman et al. | |
| 4,496,538 | 1/1985 | Gordon | 424/92 |
| 4,619,828 | 10/1986 | Gordon | |
| 4,644,059 | 2/1987 | Gordon | 424/88 |
| 4,686,102 | 8/1987 | Ritchey et al. | |
| 4,695,624 | 9/1987 | Marburg et al. | 530/395 |
| 4,707,543 | 11/1987 | Zollinger et al. | |
| 4,711,779 | 12/1987 | Porro et al. | |
| 4,727,136 | 2/1988 | Jennings et al. | 530/395 |
| 4,755,381 | 7/1988 | Cryz | 424/92 |
| 4,830,852 | 5/1989 | Marburg et al. | 424/85.8 |
| 4,882,317 | 11/1989 | Marburg et al. | 514/54 |
| 5,006,335 | 4/1991 | Glück et al. | 424/89 |
| 5,034,519 | 7/1991 | Beuverby et al. | |
| 5,091,300 | 2/1992 | Hurni et al. | 435/5 |

FOREIGN PATENT DOCUMENTS

| | | |
|---|---|---|
| 0038265A1 | 10/1981 | European Pat. Off. ....... A61K 39/09 |
| 041897A3 | 12/1981 | European Pat. Off. . |
| 098581A2 | 1/1984 | European Pat. Off. . |
| 097407A1 | 1/1984 | European Pat. Off. . |
| 0157899A3 | 10/1985 | European Pat. Off. ....... A61K 39/09 |
| 0611188A3 | 11/1985 | European Pat. Off. ....... C07K 17/06 |
| 0208375A2 | 1/1987 | European Pat. Off. ..... A61K 39/116 |
| 0338265 | 10/1989 | European Pat. Off. . |
| 497524A2 | 5/1992 | European Pat. Off. . |
| 0186576A2 | 7/1986 | Japan ........................... C07K 17/10 |
| 2102291 | 2/1983 | United Kingdom . |
| WO87.06267 | 10/1987 | WIPO . |

OTHER PUBLICATIONS

J. G. Howard et al., Immunology, 1971, 21, pp. 535–546.
P. Chabrecek et al., Chromatographia, Aug. 1990, 30, pp. 201–204.
E. A. Kabat and A. E. Bezer, Archives of Biochemistry and Biophysics, 78 pp. 306–318. (1958).
O. Makela et al., Scand. J. Immunol., 19, 541–550, 1984.
Gerald Zon et al., Infect. Immun., 37, pp. 89–103, Jul. 1982.
Manssur Yalpani, Studies in Org. Chem., 36, pp. 371–405, 1988.
S. Marburg et al., Am.Chem.Soc., 108, pp.5282–5287, 1986.
M. Porro et al., J. of Bio. Standarization, 11; pp. 65–74 (1983). "Immuno electrophoretic characterization of the Molecular Weight Polydispersion of Polysaccharides in multivatent . . . ".
H. Snippe et al., Infec. and Immunity, 42; No. 2, pp. 842–844 (1983). "Preparation of a Semisynthetic Vaccine to *Streptococcus pneumoniae*, Type 3".
Ali Fattom et al. Infec. and Immunity, 58; No. 7, pp. 2309–2312 (1990. "Serum Antibody Response in Adult Volunteers Elicited by Injection of . . . . "
Howard, J.G. et al. Immunology, 21: pp. 535–546 (1971).
Pediatric Research, 29:179A (1991).
Lifely, M. R. et al. Vaccine, 9: 60–66 (1991):
Frasch, C. E. et al. The Journal of Infectious Diseases, 158: 710–718 (1988).
The Journal of Infectious Diseases, 165: 152–155 (1992).

Primary Examiner—Kay K. A. Kim
Attorney, Agent, or Firm—Joanne M. Giesser; Jack L. Tribble

[57] ABSTRACT

A novel conjugate vaccine comprising partially hydrolyzed, highly purified, capsular polysaccharide (Ps) from *Streptococcus pneumoniae* bacteria (pneumococci, Pn) linked to an immunogenic carrier protein, is produced by a new process. The conjugate is useful in the prevention of pneumococcal infections. Vaccines comprising a mixture of from one to ten different pneumococcal polysaccharide-immunogenic protein (Pn-Ps-PRO) conjugates induce broadly protective recipient immune responses against the cognate pathogens from which the polysaccharide components are derived. Young children and infants younger than 2 years old, normally unable to mount a protective immune response to the Pn-Ps alone, exhibit protective immune responses upon vaccination with these Pn-Ps-PRO conjugates.

10 Claims, No Drawings

PNEUMOCOCCAL POLYSACCHARIDE CONJUGATE VACCINE

RELATED CASES

This is a continuation of application Ser. No. 07/807,942 filed on Dec. 19, 1991, now abandoned, which is a continuation-in-part of application U.S. Ser. No. 646,570, filed on 28 Jan. 1991, now abandoned.

BACKGROUND OF THE INVENTION

The pathogenic bacteria classified as *Streptococcus pneumoniae* (pneumococci, Pn) have been subdivided into 84 antigenic serotypes, based on the capsular polysaccharide (Pn-Ps) of the organism. Disease states attributable to these organisms include pneumonia, meningitis, otitis media, bacteremia and acute exacerbations of chronic bronchitis, sinusitis, arthritis and conjuctivitis. The preponderance of these diseases, however, are caused by a limited subset of the 84 known isolates. Thus a polyvalent vaccine containing the Pn-Ps from the most prevalent and pathogenic isolates of the organism can provide protection against a very high percentage of the most frequently reported pathogens of this class.

Polyvalent vaccines have been produced that are efficacious in raising protective immune responses against the pneumococci in adults. "PNEUMOVAX® 23" (Pneumococcal Vaccine Polyvalent, MSD; see PDR, 1990 edition, p. 1431), for example, is a liquid composition containing 50 μg/ml of each of the 23 different, unconjugated pneumococcal polysaccharides, all of which are on deposit with the ATCC and provid one possible source of starting material for this invention. "PNEUMOVAX® 23" comprises each of the following free, that is unconjugated, polysaccharides: 1, 2, 3, 4, 5, 6B, 7F, 8, 9N, 9V, 10A, 11A, 12F, 14, 15B, 17F, 18C, 19F, 19A, 20, 22F, 23F and 33F, accounting for about 90% of pneumococcal blood isolates. However, such vaccines are least effective in the segment of the population most at risk for pneumococcal infections: B-Cell immunocompromised individuals, the elderly and infants younger than two years old who depend on T-cell responses for immune protection. Since unconjugated polysaccharides are poor inducers of T-cell immune responses, conversion of the Pn-Ps into immunogens capable of inducing T-cell responses is the key to producing adequate protection in this target population. Use, however, is not restricted to this group of individuals. For example, administration of a vaccine, comprising one or more of the novel conjugates, to a female mammal prior to or during pregnancy raises antibodies in the mother which can passively protect a developing fetus and suckling infant even though the vaccine is not administered directly to the fetus or infant. Such conjugate vaccines should also prove useful for eliciting antibodies for ultimate passive protection of at risk populations, such as newborns or siblings of infected individuals.

Polysaccharides found to be poorly immunogenic by themselves have been shown to be quite good immunogens once they are conjugated to an immunogenic protein, PRO, [Marburg et al., U.S. Pat. No. 4,695,624; Schneerson et al., *New Dev. with Hum. & Vet. Vaccines*, 77–94 (1980); Schneerson, et al., *J. Exptl. Med.*, 152, 361 (1980); Anderson, *Infection and Immunity*, 39, 233 (1983)]. However, a major problem in the production of such conjugates is the viscous and non-homogenous nature of the polysaccharide starting material and hence the difficulty in defining the conjugate product chemically. Thus, a process is required wherein the starting materials are as well defined as possible and each step in the synthetic route is assayable as to intermediate formed. The process herein disclosed satisfies this requirement by providing highly immunogenic conjugate immunogens against the cognate pathogens from which the Pn-Ps is derived. The conjugates are useful in infants younger than two years old.

Marburg et al., [*J. Am. Chem. Soc.*, 108, 5282 (1986), and U.S. Pat. Nos. 4,695,624; 4,830,852; 4,882,317] disclosed a means of conjugating polysaccharides and immunogenic proteins through bigeneric spacers. The PRO was derivatized to exhibit pendant nucleophilic or electrophilic groups (PRO*), while a partner Ps was functionalized so as to exhibit pendant groups of opposite reactivity (Ps*). Upon combining Ps* with PRO*, bigeneric spacers were formed, covalently joining Ps to PRO (Ps-PRO). Upon acid hydrolysis, the bigeneric spacer is released as an unusual amino acid, quantitated by amino acid analysis, and thereby providing a means of proving covalency.

This invention discloses a process improved over that which is disclosed in U.S. Pat. Nos. 4,695,624; 4,830,852; 4,882,317. The improvements include preparation of Pn-Ps starting material having more specific, reproducible and manageable physical properties than provided by crude Pn-Ps preparations, including: increased solubility, increased filterability, increased purity (reduction in contamination with group specific C-polysaccharide (C-Ps), and reduced molecular weight, polydispersity and viscosity. The resultant conjugates disclosed herein are improved over those provided by the U.S. Pat. No. 4,695,624 process with respect to increases in the consistency and ease of preparation, improved antigenicity and improved purity of the final product. Especially significant is the 3–20 fold reduction of group specific C-polysaccharide and peptidoglycan in the pre-conjugation Pn-Ps relative to the pre-conjugation Ps preparations of the U.S. Pat. No. 4,695,624 patent. Although the presence of the C-polysaccharide contaminant does not interfere with the immune responses against the type specific antigens, C-Ps could participate in the conjugation reaction rendering it less specific and controlled for the type-specific Ps. Furthermore, production of anti-C-polysaccharide antibodies may correlate with the tissue destruction observed in some unresolved pneumococcal infections.

In addition to the novel conjugate product, this invention discloses a new process for preparing partially hydrolyzed, highly purified pneumococcal polysaccharide intermediates, novel compositions comprising from one to ten different conjugates and methods of using the invention. Of particular interest are the capsular polysaccharides included in "PNEUMOVAX® 23" (Pneumococcal Vaccine Polyvalent, MSD; see PDR, 1990 edition, p. 1431). A most preferred subset are the capsular polysaccharides of *Streptococcus pneumoniae* subtypes 6B, 23F, 19F, 14, 18C, 4 and 9V, as this small group of pneumococcal subtypes are estimated to be responsible for between 75–85% of pneumococcal infections in infants and children. The methods provided herein are applicable to a broad collection of pneumococcal and other bacterial polysaccharides.

SUMMARY OF THE INVENTION

Highly chemically defined pneumococcal polysaccharide (Pn-Ps) is prepared by partially-hydrolyzing a crude Pn-Ps preparation to an endpoint predetermined to maintain the antigenic integrity of the Pn-Ps. The partially hydrolyzed Pn-Ps is purified substantially and is useful for the preparation of Pn-Ps-immunogenic protein (PRO) conjugates (Pn-Ps-PRO).

Novel and highly antigenic Pn-Ps-PRO conjugates of the invention, comprising the outer membrane protein complex (OMPC) or *Neisseria meningitidis* b, or recombinant or purified subunits thereof, such as MIEP, or other immunogenic carrier proteins covalently linked to partially hydrolyzed and highly purified Pn-Ps intermediates from prevalent pneumococcal isolates, are useful for prevention of pneumococcal infections in mammals. The conjugates are particularly useful in vaccine compositions for stimulating anti-pneumococcal immune responses in mammals, especially in B-cell immunocompromised individuals, the elderly and in human infants younger than two years old, as the conjugates elicit T-cell responses. Pn-Ps-OMPC and Pn-Ps-MIEP conjugates are made by a process comprising the steps of: isolating capsular Ps from cultures of *Streptococcus pneumoniae* (pneumococci, Pn), partially hydrolyzing or physically shearing the Pn-Ps, fractionating said Pn-Ps, to yield a Pn-Ps product of reduced molecular size, polydispersity, viscosity and then covalently conjugating the Pn-Ps to OMPC or MIEP.

OBJECTS OF THE INVENTION

It is an object of this invention to provide novel, partially-hydrolyzed and highly purified antigenically type-specific pneumococcal capsular polysaccharides (Pn-Ps), useful as intermediates in the preparation of T-cell dependent conjugates of the Pn-Ps and immunogenic proteins. Another object is to provide T-cell dependent conjugates of the Pn-Ps and immunogenic proteins, useful in vaccine compositions to prevent pneumococcal infections, especially in infants younger than two years old and in B-cell immunocompromised people. Another object is to provide a process, improved over that provided in U.S. Pat. No. 4,695,624, for the formation of covalent pneumococcal polysaccharide-immunogenic protein conjugates (Pn-Ps-Pro), wherein the improvement consists of greater chemical definition and purity of the starting Pn-Ps, intermediates, final product and increased consistency and ease in carrying out the process itself. Another object is to provide chemically defined Pn-Ps-PRO conjugates, according to the improved process, demonstrating T-cell dependency, useful in eliciting protective serum antibody against pathogenic pneumococci, especially in infants younger than 2 years old and in immunocompromised individuals. Another object is to provide a method of treatment, employing these conjugates in immunologically-effective amounts in vaccine formulations, to prevent pneumococcal induced diseases such as otitis media, meningitis, pneumonia, bacteremia and the acute exacerbations of chronic arthritis, sinusitis, bronchitis and conjunctivitis.

DETAILED DESCRIPTION OF THE INVENTION

A. The Novel Pn-Ps-PRO Conjugate and Polysaccharide Intermediates:

The Pn-Ps-PRO conjugate product of this invention has a Pn-Ps to PRO ratio between 0.05 and 0.5 mg polysaccharide/mg protein, a high degree of covalency, minimal contamination of the conjugate by free Pn-Ps and unique physical and chemical characteristics endowed by the novel constituent polysaccharides.

The conjugate comprises an immunogenic protein (PRO) covalently coupled through a spacer to a novel, partially hydrolyzed and highly purified pneumococcal capsular polysaccharide (Pn-Ps). The immunogenic protein is preferably the outer membrane protein complex (OMPC) derived from a culture of *Neisseria meningitidis* b. One method for preparing OMPC is essentially as provided in U.S. Pat. No. 4,271,147 and Example 1. Alternatively, a subunit of OMPC, such as MIEP, produced by dissociation of the OMPC or by recombinant expression thereof, is also preferred. One method of achieving this objective is provided in patent application U.S. Ser. Nos. 555,978; 555,329 and 555,204 (Merck Case #'s 18110, 18159 and 18160 respectively, filed on Jul. 19, 1990) and Example 2, 16–23.

The novel partially hydrolyzed and highly purified pneumococcal capsular polysaccharide (Pn-Ps) is a preparation of an antigenic polysaccharide derived from a culture of one of the pneumococcal subtypes (as described below in the section describing a novel conjugation process and in Examples 3–10). The Pn-Ps has an average molecular weight between about $1 \times 10^5$ and $1 \times 10^6$ daltons, on average less than about 1000 repeating units per molecule, a C-polysaccharide contamination level of less than about 3% and an antigenicity index between 0.4 and 1.1, and preferably between 0.7 and 1.1. This last parameter is the relative amount of anti-pneumococcal type-specific antibody binding exhibited per unit mass of the new Pn-Ps as compared with crude Pn-Ps on deposit with the ATCC. Furthermore, the novel Pn-Ps is amenable to conjugation with immunogenic protein to produce the Pn-Ps-PRO product of the invention. Some physical and chemical characteristics of 2 different Pn6B-Ps and 2 different Pn23F-Ps preparations are given in Table I below, while the description that follows reveals how those characteristics are measured. The process disclosed below provides a method for making Pn-Ps intermediates and Pn-Ps-PRO conjugates with a wide variety of pneumococcal subtypes, including but not restricted to those selected from subtypes 1, 2, 3, 4, 5, 6B, 7F, 8, 9N, 9V, 10A, 11A, 12F, 14, 15B, 17F, 18C, 19F, 19A, 20, 22F, 23F and 33F. As mentioned above, a preferred subset of pneumococcal polysaccharides are those derived from pneumococcal subtypes 4, 6B, 9V, 14, 18C, 19F and 23F. It wil be obvious to those skilled in the art that in addition to or in place of any of these polysaccharides, others may be substituted as the need arises in the at-risk polulation. Thus, Pn1-Ps and Pn5-Ps may be treated like Pn4-Ps or Pn9V-Ps, as could *Neisseria meningitidis* B, C, or Group B Streptococcal polysaccharides, while Pn7F-Ps may be treated like Pn14-Ps, as further described below, and included in a multivalent vaccine. It will also be clear to those skilled in the art that by inclusion of Pn6B-Ps, protection against Pn6A would be provided by cross-reactive antibodies. This is also true for a number of other pneumococcal subtypes.

Multivalent vaccines are those comprising mixtures of different Pn-Ps-PRO conjugates each prepared separately with a given Pn-Ps subtype. In addition, multivalent vaccines are those wherein several different Pn-Ps subtypes are all conjugated to a given PRO at one time or sequentially.

1. Characterization of the Novel Polysaccharide Intermediates:

The physical and chemical characteristics of the partially hydrolyzed, purified pneumococcal capsular polysaccharide intermediates depend on the pneumococcal subtype from which it was derived and the manipulations they undergo according to the process disclosed herein. In general, the Pn-Ps intermediates have a 2–10 fold lower molecular size and polydispersity as compared with crude bacterial culture derived polysaccharide. The reduced size allows for improved polysaccharide handling during conjugation and post-conjugation removal of free Pn-Ps, higher Pn-Ps purity/homogeneity, lower Pn-Ps molecular-size polydispersity and essentially unaltered antigenicity. These novel Pn-Ps characteristics contribute significantly to the consistent formation of a highly defined, highly type-specific, antigenic Pn-Ps-PRO product.

i. Pn-PS Molecular Weight and Polydispersity:

By measuring the weight-average molecular weight, $M_W$, by a diffusion, sedimentation or chromatographic means and the number-average-molecular weight, $M_N$, by a colligative property such as viscosity, freezing-point-depression or boiling-point-elevation, the polydispersity of the Pn-Ps preparation is obtained as the ratio $M_W/M_N$. The closer this number approaches unity, the more homogeneous the polysaccharide preparation. The polydispersity of a number of Pn-Ps preparations is given herein and a preferred process for achieving this enhanced homogeneity is also disclosed.

The partition coefficient, $$K_d = \frac{Ve - Vo}{Vi - Vo}$$

Vo = column void volume.
Vi = total permeation volume.
Ve = elution volume of sample.
$K_d$ = partition coefficient of the sample of each crude and partially-hydrolyzed Pn-Ps preparation is measured by size-exclusion chromatography (SEC), or high-performance size-exclusion chromatography (HPSEC), of an aliquot of polysaccharide, according to methods known in the art. The $K_d$ thus obtained is a measure of the average hydrodynamic volume of the polysaccharide preparation. As the molecular size of the Pn-Ps is reduced by physical shear or by thermal or sonic hydrolysis according to the disclosed process, the elution volume, $V_e$, of the Pn-Ps increases and so does the $K_D$.

A preferred column matrix for this purpose is SEPHAROSE CL2B gel (Pharmacia No. 17-0120-01). The column void volume (VO) is determined with Blue Dextran 2000 (Pharmacia No. 17-0360-01) and the total permeation volume (Vi) from a sodium chloride salt peak. According to one method, the Pn-Ps sample is prepared at 2.5 mg/mL in distilled water and a 1-mL injection volume is used. The ratio $V_o/V_i$ should be in the range of 0.32–0.37. The $k_d$ for Dextran T500 (Pharmacia No. 17-0320-01) should be between 0.37–0.49. A preferred HPSEC system includes a 7.5×600 mm TSK G6000 PW column heated to 50° C.

In a highly preferred method, SEC or HPSEC is combined with a differential refractometer, which monitors relative analyte concentration as a function of elution volume and a differential viscometer, which monitors the specific viscosity of the analyte as a function of elution volume. A universal calibration curve [log (intrinsic viscosity times molecular weight) versus retention volume] is constructed from analysis of a series of monodisperse polyethylene oxide standards. The concentration and specific viscosity profiles can be used to calculate a molecular weight versus elution volume profile for the sample, which in turn is used to calculate the values for $M_n$ and $M_w$, from which the polydisperisty index ($M_w/M_n$) is calculated [Yau, W. W. and Rementer, S. W., *J. Liq. Chromatog.*, 13, 627–675 (1990); Nagy, *J. Liq. Chrom.*, 13, 677–691 (1990); Benoit, et al., *J. Ch. Phys. Tome.*, 63, 1507–1514 (1966)]. In the present invention, intrinsic viscosity was measured in 0.1M sodium phosphate buffer, pH 7.2.

Once the average molecular weight of a Pn-Ps preparation has been determined, the average number of repeating units per molecule is easily determined by dividing the polymer molecular weight by the molecular weight of the repeating unit (see Table II).

ii. Retention of Pn-PS Type-Specific Antigenicity:

It is important, for each crude Pn-Ps subjected to physical shear or chemical, thermal, sonic or enzymatic hydrolysis, that an end-point be established at which antigenic integrity begins to dissipate. This end-point is conveniently established by correlating viscosity with any of a number of immunologic tests known in the art. In a preferred method, an aliquot of polysaccharide solution is measured by the Ouchterlony double immunodiffusion assay using pneumococcal subtype-specific antibody. Appearance of a white precipitin band in the agar which joins the precipitin band of a sample of crude Pn-Ps placed in an adjacent well after a period of diffusion, provides qualitative identity of reactants, and evidence that the polysaccharide's antigenic integrity remains intact. A more quantitative immunological assay is achieved by rate nephelometry analysis or an RIA.

Rate Nephelometry measures the change or the rate of change in the intensity of light scattered during formation of antigen-antibody complexes. The reaction is run in a reaction cell through which a beam of light is passed. In the present case, the complexes are formed by an immunoprecipitin reaction that occurs in solution when a specific antibody (Ab) reacts with its specific antigen (Ag), i.e., Pn-Ps. Because the formation of an Ag-Ab complex is dependent upon the presence of Ag and Ab molecules in optimal proportions, the degree of complex formation for a constant amount of Ab increases with the amount of Ag up to a maximal level; larger amounts of Ag result in less complex being formed. Thus, by maintaining a constant level of Ab and measuring the light scatter with increased concentrations of Ag, a standard curve is generated. It is possible to calculate the Ag concentration for a Ps (or derivatized Ps) preparation when samples are reacted with their specific Ab under the same conditions used to develop the standard curve.

A comparison of the concentration calculated immunologically by rate nephelometry with the concentration obtained chemically or physically (by colorimetry, refractive index or by total hydrolysis and quantitation of monosaccharides—see below) gives as index of antigenicity for the Ps samples. Dry weight analysis of polysaccharides is only appropriate if the volatile content of the powder preparation is known. Polysaccharides are notoriously hygroscopic and may contain anywhere from 5 to 30% by weight of volatiles. As such, dry weight measures in and of themselves are not particularly reliable. One method used for determining polysaccharide concentration with reasonable accuracy is by colorimetric assay, where the assay is calibrated with a standard solution of the polysaccharide of interest. For example, Pn6B-Ps, Pn18C-Ps, Pn19F-Ps and Pn23F-Ps may all be quantitated by the methyl pentose assay of Dische and Shettles [*J. Biol. Chem.*, 175, 595–603 (1948)]. Pn4-Ps, Pn9V-Ps, Pn14-Ps and Pn19F-Ps may be quantitated by the hexosamine content and Pn9V may also be quantitated by uronic acid content. The Phenol-Sulfuric acid assay [Dubois et al., *Anal. Chem.*, 28, 350–356 (1956)] is useful for quantitating all of these Pn-Ps preparations as part of in-process testing during conjugate preparation. The other method employed is to use a refractive index signal as a measure of analyte mass, also calibrated with a standard solution of the polysaccharide of interest. Though the colorimetric assay is used for monitoring the polysaccharide content of the samples during the derivatization and conjugation process, the latter method is used during the physical characterization of the polysaccharide preparation by HPSEC-universal calibration analysis and for calculation of the antigenicity index. Starting crude Pn-Ps is assigned an antigenicity index value of 1.0. An index of relative antigenicity is calculated for experimental samples and a value of 0.4–1.1 is considered satisfactory. It is possible to get an antigenicity index of greater than 1.0 if the polysaccharide is significantly purified during the hydrolysis and fractionation step. It is also theoretically possible that size reduction alone could increase the antigenicity index of a preparation by increasing the flexibility of the polysaccharide molecules and thus decreasing steric interference around the antigenic epitopes. These determinations are performed as an in-process check for hydrolyzed, fractionated and derivatized Ps samples. Samples which have relative antigenicities of <0.4 are rejected, i.e., not conjugated. Anti-Pn-Ps antibody preparations are available that are useful in characterizing pneumococcal polysaccharides. Sources of anti-Pn-Ps antibodies include the Health Research, Inc., Albany, N.Y., and the Staten Serun Institute. Alternatively, type-specific anti-Pn-Ps antibodes may be prepared for this purpose according to methods known in the art using commercially available crude Pn-Ps as the immunogen [Baker et al., *Immunology* 20, 469 (1971); Brooke, M. S., *J. Immunol.*, 95, 358 (1966); Kearney, R. and Halladay, W. J., *Aust. J. Exp. Biol. Med. Sci.*, 48, 227 (1970); Schneerson, R. et al., *Prog. Allergy*, 33, 144 (1983); Robbins, J. B., *Infect. Immun.*, 26 1116 (1979)].

A further indication of retained antigenic integrity is the maintainance of the correct chemical composition of Pn-Ps preparation. For Example, Pn6B-Ps has a repeat unit of [α-Gal(1-3)-α-Glu(1-3)-α-L-Rhap(1-4)-D-Ribitol-5-$PO_4(_2)$] so that the mole ratio of the carbohydrate components ribitol:rhamnose:galactose:glucose is approximately= 1:1:1:1. This ratio may be determined, for example, upon hydrolysis of the polysaccharide with 36% hydrofluoric acid for about 2 hours at 45°–65° C. followed by 2M trifluoroacetic acid for 10–20 hours at 100° C. and high performance anion exchange chromatography with pulsed amperometric detection. Four peaks, representing approximately equal molar amounts of the carbohydrate components, is thus an indication of maintained integrity. Essentially theoretical ratios of carbohydrate components are maintained for all the novel Pn-Ps compounds of this invention, within about 20%. The departures from theoretical values is primarily due to limitations in the art of the method. Thus, upon total hydrolysis: Pn23F-Ps has a ratio of about glycerol:rhamnose:galactose:glucose=1:2:1:1; Pn14-Ps has a ratio of about N-acetyl-glucosamine:galactose:glucose=1:2:1; Pn19F-Ps has a ratio of about rhamnose:N-acetyl-mannosamine:glucose=1:1:1; Pn18C-Ps has a ratio of about glucose:galactose:rhamnose:glycerol:acetate=3:1:1:1:1; Pn9V-Ps has ratio of about glucose:galactose:N-acetyl-mannosamine:glucuronic acid:galacturonic acid:acetate=2:1:1:1:1.7; and Pn4-Ps has a ratio of about N-acetyl-mannosamine:N-acetyl-fucosamine:galactosamine:galactose:pyruvate= 1:1:1:1:1. In addition, Pn4-Ps has recently been found to contain an additional component, identified by HPLC analysis, which appears to be 2-aminopneumosamine (2-amino-2,6-dideoxytalose), as does Pn5-Ps [Barker et al., *Carbohydrate Res.*, 224–233 (1966)]. Pn19F-Ps also has an additional component, probably a hexosamine, which has not been reported in the literature, and for which definitive identification is still pending. These and additional theoretical polysaccharide repeat compositions are reported in the following references: J. E. G. van Dam et al., *Carbohyd. Res.* 187, 267 (1988); H. J. Jennings, *Adv. Carbohd. Chem.* 41, 155 (1983) and references therein; J. C. Richards and M. Perry, *Biochem. Cell. Biol.* 66, 758 (1988). In addition to the carbohydrate components, there are phosphate, acetate, and pyruvate sidegroups in several of the Pn-Ps of interest, with some of these being immunodominant features. As such, these components may also be monitored (see Example 30). Quantitation of monosaccharides is also a useful means for quantitating the polysaccharide concentration of a sample.

A further element in the antigenicity of the subject polysaccharides is the maintainance of what has been called a "conformational epitope" in the polysaccharide [See for example Wessels, M. R. and Kasper, D. L., *J. Exp. Med.*, 169, 2121–2131 (1989)]. This level of antigenicity appears to be expressed only in high molecular weight forms of the saccharide, and the methods described herein are directed at preservation of this level of polysaccharide immunogenicity also.

iii. Minimal Contamination by C-Polysaccharide:

Another critical parameter is the level of C-polysaccharide contamination. This value may be shown by total acid hydrolysis of a polysaccharide preparation, chromatography of the hydrolysate and conductometric detection of choline [Hermans, et al., *Recl. Tray. Chim. Pays-Bas*, 107, 600 (1988)]. Alternatively, the non-hydrolyzed polysaccharide may be analyzed by NMR for choline. The NMR technique uses the ratio of the choline signal to the rhamnose methyl signal (for Pn-Ps containing a rhamnose; a different signal for other Pn-Ps) for calculating the C-Ps content. The chromatographic method uses the ratio of the choline signal to either the polysaccharide content determined by conductometric assay or to one of the Pn-Ps component peaks to calculate the C-Ps content. In either method, standards of known concentrations of choline allow direct calculation of the level of choline present in a polysaccharide preparation using the theoretical repeat structure of C-Ps (Herman et al. [full ref. above], the concentration of C-Ps in a polysaccharide preparation is determined. Polysaccharide concentrations of Pn-Ps samples are measured according to methods known in the art. For example, total polysaccharide concentration may be determined by total hydrolysis of the polysaccharide and measurement of the concentration of a specific monosaccharide. By comparing the C-Ps concentration to total polysaccharide concentration, the degree of C-polysaccharide contamination (W/W) is determined. Levels of C-polysaccharide below 3% (w/w) of total polysaccharide are considered acceptable but even more preferrable are levels below 1%.

Chemical and physical properties of two lots of Pn6B-Ps and two lots of Pn23F-Ps are summarized in Table I below. These data show the reproducibility of lot to lot parameters resulting from the novel process described herein:

TABLE I

| Characteristics of Hydrolyzed and Fractionated Pn-Ps | | | | |
|---|---|---|---|---|
| Pn-Ps Preparation | 6B-1 | 6B-2 | 23F-1 | 23F-2 |
| Viscosity End Pt | 1.094 | 1.147 | 1.350 | 1.376 |
| Kd (HPSEC) | 0.62 | 0.62 | 0.49 | 0.49 |
| Kd (CL-2B) | 0.64 | 0.60 | 0.41 | N.D. |
| Monosaccharide | S | S | S | S |
| Antigenicity: | | | | |
| Ouchterlony | S | S | S | S |
| Nephelose | S | S | S | S |
| (Phenol:Sulfuric) | S | S | S | S |

S: Satisfactory

In Table II below, chemical and physical parameters of several crude pneumococcal polysaccharides and of the corresponding novel hydrolyzed and fractionated (Hyd+ frac) compounds of this invention are shown. Numbers presented are approximate within experimental error and limits of detection for the complex polysaccharide compounds being prepared.

TABLE II

PHYSICAL AND CHEMICAL CHARACTERISTICS OF CRUDE AND OF NOVEL HYROLYZED + fractionated Pn-Ps COMPOUNDS

| Pn-Ps Substype | Peak $K_d$ | Intrinsic Viscosity | Weight Avg. Mol. Wt. ($M_W$) | Number Avg. Mol Wt. ($M_N$) | Polydispersity ($M_W/M_N$) | Number of Repeating units per molecule | C-Ps % |
|---|---|---|---|---|---|---|---|
| 4-crude | 0.55 ± 0.05 | 4.34 ± 10% | $4.2 \times 10^5 \pm 20\%$ | $3.3 \times 10^5 \pm 20\%$ | 1.2–1.6 | >600 | >3 |
| 4-hyd + frac | 0.69 ± 0.05 | 1.0–3.0 | $1 \times 10^5 – 5 \times 10^5$ | $2 \times 10^5 – 4 \times 10^5$ | 1.0–1.4 | <600 | <3 |
| 6B-crude | 0.40 ± 0.05 | 2.67 ± 10% | $1.4 \times 10^6 \pm 20\%$ | $9 \times 10^5 \pm 20\%$ | 1.5–2.5 | >1000 | >3 |
| 6B-hyd + frac | 0.60 ± 0.05 | 1.0–2.0 | $3 \times 10^5 – 7 \times 10^5$ | $3 \times 10^5 – 6 \times 10^5$ | 1.0–1.4 | <1000 | <3 |
| 9V-crude | 0.53 ± 0.05 | 2.29 ± 10% | $1.1 \times 10^6 \pm 20\%$ | $9 \times 10^5 \pm 20\%$ | 1.2–2.5 | >800 | >3 |
| 9V-hyd + frac | 0.65 ± 0 05 | 1.0–2.0 | $3 \times 10^5 – 7 \times 10^5$ | $3 \times 10^5 – 6 \times 10^5$ | 1.0–1.4 | <800 | <3 |
| 14-crude | 0.50 ± 0.05 | 1.69 ± 10% | $1.1 \times 10^6 \pm 20\%$ | $7 \times 10^5 \pm 20\%$ | 1.3–2.5 | >1200 | >3 |
| 14-hyd + frac | 0.60 ± 0.05 | 0.6–1.6 | $4 \times 10^5 – 1 \times 10^6$ | $3 \times 10^5 – 8 \times 10^5$ | 1.0–1.4 | <1200 | <3 |
| 18C-crude | 0.50 ± 0.05 | 5.20 ± 10% | $8.7 \times 10^5 \pm 20\%$ | $6 \times 10^5 \pm 20\%$ | 1.4–2.5 | >700 | >3 |
| 18C-hyd + frac | 0.65 ± 0.05 | 1.5–3.0 | $2 \times 10^5 – 6 \times 10^5$ | $2 \times 10^5 – 6 \times 10^5$ | 1.0–1.4 | <700 | <3 |
| 19F-crude | 0.44 ± 0.05 | 2.95 ± 10% | $1.0 \times 10^6 \pm 20\%$ | $6 \times 10^5 \pm 20\%$ | 1.8–2.5 | >1000 | >3 |
| 19F-hyd + frac | 0.65 ± 0.05 | 1.0–2.0 | $2 \times 10^5 – 6 \times 10^5$ | $2 \times 10^5 – 6 \times 10^5$ | 1.0–1.4 | <1000 | <3 |
| 23F-crude | 0.36 ± 0.05 | 4.15 ± 10% | $2.2 \times 10^6 \pm 20\%$ | $1 \times 10^6 \pm 20\%$ | 2.0–3.0 | >1000 | >3 |
| 23F-hyd + frac | 0.54 ± 0.10 | 1.5–3.0 | $4 \times 10^5 – 8 \times 10^5$ | $2 \times 10^5 – 6 \times 10^5$ | 1.0–1.4 | <1000 | <3 |

2. Characterization of the Novel Pn-Ps-PRO Conjugate:

i. Analysis of identity and quantity of Pn-Ps:

It is very useful to verify the quantity and chemical integrity of Pn-Ps in a final conjugate by an independent technique to assure antigenicity (integrity) and calculate the Pn-Ps/PRO ratio. One method includes total hydrolysis using 2M TFA at 100° C. for 5–16 hours, depending on the optimal hydrolysis time for each particular Pn-Ps. Equal amounts of Pn-Ps-PRO conjugate and PRO hydrolysate (based on Lowry protein) are analyzed by high-performance anion exchange chromatography with pulsed amperometric detection to obtain monosaccharide profiles. The profile of PRO is "subtracted" from the profile of the Pn-Ps-PRO conjugate using appropriate computer software such as the Nelson program, in order to correct for monosaccharides contributed by PRO, for example, from lipopolysaccharide (LPS) present in OMPC. The quantity of Pn-Ps in the conjugate is then calculated by comparing the profile of the known amount of the derivatized Pn-Ps hydrolysate and the corrected Pn-Ps-PRO conjugates. The Pn-Ps/PRO ratio is also measured in this manner.

ii. Analysis for novel amino acids indicative of conjugation and capping

Following conjugation of Pn-Ps to PRO, samples of the conjugate are hydrolyzed in 6N HCl and subjected to amino acid analysis. This method detects the presence and amount of unique amino acids such as S-carboxymethyl-homocysteine (S-CMHC) and S-carboxymethyl cysteamine (S-CMCA). The former amino acid is created as part of the chemical link by the chemical reaction between derivatized Pn-Ps and PRO as described in the process section below and is taken as definitive proof of the covalent linkage of derivatized Pn-Ps to PRO. Formation of such a covalent linkage is essential to the T-cell immunogenicity of the conjugate vaccine. Immediately following completion of the conjugation reaction, unreacted bromoacetamide moeities are capped with N-acetyl cysteamine. Hydrolysis of this linkage results in the release S-carboxymethyl cysteamine (S-CMCA), also detected in the Amino Acid Analysis. Detection of this amino acid confirms successful capping of the reactive bromoacetomide groups, thus making them unavailable for any unwanted chemical reactions. Acceptable levels of covalency and capping are between about 1–15% for S-CMHC/Lys and about 0–5% for S-CMCA/Lys.

iii. Analysis of the Aluminum Hydroxide-Adsorbed Vaccine:

In a preferred embodiment, the Pn-Ps-PRO conjugate is absorbed to aluminum-hydroxide (alumina, $Al(OH)_3$ gel (see section C. below) resulting in a potentiation of the immune response to the vaccine. Other possible vaccine formulation include formulation in physiologically acceptable diluants and the use of other adjuvants, immunomodulators or inert excipients other than the aluminum hydroxide gel. Analysis of this alumina-absorbed material is provided for as follows.

The alumia adsorbed Pn-Ps-PRO can be analyzed for composition and stability following desorption of the conjugate from alum. This is accomplished by dialyzing the alumina-adsorbed Pn-Ps-PRO against a 3% sodium citrate solution for 16 hours at room temperature. The resulting soluble aluminum citrate salt migrates out of the dialysis membrane and leaves behind the Pn-Ps-PRO. This method is important in order to confirm that the correct amount of Pn-Ps-PRO is in the alumina-adsorbed formulation. However, some formulations such as Pn6B-Ps-OMPC and Pn23F-Ps-OMPC contain 10, 5, 2 and 1 meg Pn-Ps/mL (see section C. below), concentrations well below chemical detection methods. Therefore, in order to perform carbohydrate compositional analyses the adsorbed Pn-Ps-OMPC vaccines first are pelleted to remove the aqueous fluid and the pellet resuspended in one-fifth of the original volume prior to citrate dissolution. Following dialysis, the solubilized Pn-Ps-OMPC is present at 50, 25, 10 and 5 mcg Pn-Ps/mL. These concentrations are then amenable to both Pn-Ps and protein analysis to confirm dosage levels.

Citrate-desorbed samples are also analyzed for the possible presence of free Pn-Ps, an issue which is important for immunogenicity and consistency of production. This analysis is performed by chromatography on a SEPHAROSE CL-2B or SEPHACRYL S1000SF sizing column in which Pn-Ps-OMPC can be separated from Pn-Ps. The presence and amount of free Pn-Ps is measured antigenically by rate nephelometry. The level of contamination of the Pn-Ps-OMPC by free Pn-Ps is less than 15% of the total Pn-Ps present.

iv. Pyrogen Test: Absence of Significant Pyrogenicity:

The conjugate product of this invention is tested for absence of adverse temperature elevation effects. Conjugate products have been produced according to the process disclosed herein and found to have acceptable levels of pyrogenicity.

Method (I.V.)

The Pn-Ps conjugate vaccine is tested as described in 21CFR, Section 610.13(b)

1) Method (I.M.)

A second measure of pyrogenicity is the rabbit IM test. This test more closely simulates use of the product in clinic and is felt to more accurately reflect the apparent endotoxin burden of the product.

Each rabbit receives 1.0 mL of vaccine by intramuscular injection. The test is performed using at least three rabbits. Temperature is monitored for five hours following injection. Other test methodologies are as described in 21 CFR Section 610.13(b). (Test dose is based on the polysaccharide concentration.)

v. Nature of the Covalent Linkage:

The Pn-Ps-PRO, such as Pn-Ps-OMPC or Pn-Ps-MIEP, conjugates may be coupled through bigeneric spacers containing a thioether group and primary amine, which form hydrolytically-labile covalent bonds with the polysaccharide and the PRO, such as OMPC or MIEP. Preferred conjugates according to this invention are those which may be represented by the formulae, Pn-Ps-A-E-S-B-PRO or Pn-Ps-A'-S-E'-B'-PRO. A-E-S-B and A'-S-E'-B' constitute bigeneric spacers which contain hydrolyrically-stable covalent thioether bonds and which form covalent bonds (such as hydrolytically-labile ester or amide bonds) with the macromolecules, PRO and Pn-Ps. In the spacer A-E-S-B, S is sulfur; E is the transformation product of a thiophilic group which has been reacted with a thiol group and is represented by

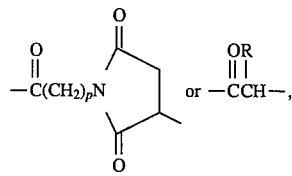

wherein R is H or $CH_3$ and p is 1 to 3; A is

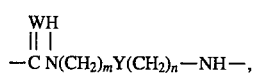

wherein W is O or NH, m is 0 to 4, n is 0 to 3 and Y is $CH_2$, O, S, NR' or $CHCO_2H$, where R' is H or $C_1$- or $C_2$-alkyl, such that if Y is $CH_2$, then both m and n cannot equal zero and if Y is O or S, then m is greater than 1 and n is greater than 1; B is

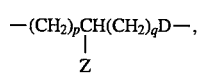

wherein q is 0 to 2, Z is $NH_2$,

COOH, or H,
where R' and p are as defined above and D is

NR', or

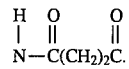

In the spacer, A'-S-E'-B', S is sulfur; A' is

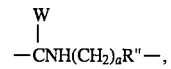

wherein a is 1 to 4 and R" is $CH_2$ or

where Y' is $NH_2$ or NHCOR' and W, p and R' are as defined above and E' is the transformation product of a thiophilic group which has been reacted with a thiol group and is represented by

wherein R is as defined above, and B' is

or E' is

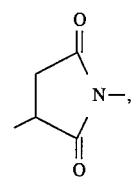

and B' is

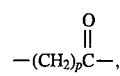

wherein p is 1 to 3. Further, of the bigeneric spacers, A-E-S-B and A'-S-E'-B', the E-S-B and A'-S-E' components are determinable and quantifiable, with this identification reflecting the covalency of the conjugate bond linking the side of the thioethersulfur which originates from the covalently-modified polysaccharide with the side of the spacer which originates from the functionalized protein.

The conjugates, Pn-Ps-A-E-S-B-PRO, according to this invention may contain spacers whose components include derivatives of, inter alia: carbon dioxide, 1,4-butanediamine and S-carboxymethyl-N-acetylhomocysteine; carbon dioxide, 1,5-pentanediamine and S-carboxymethyl-N-acetylhomocysteine; carbon dioxide, 3-oxa-1,5-pentanediamine and S-carboxymethyl-N-acetylhomocysteine; carbon dioxide, 1,4-butane-diamine and S-carboxymethyl-N-acetylcysteine; carbon dioxide, 1,3-propanediamine and S-carboxymethyl-N-benzoylhomocysteine; carbon dioxide, 3-aza-1,5-pentanediamine and S-carboxymethyl-N-acetylcysteine; carbon dioxide, 1,2-ethanediamine, glycine and S-(succin-2-yl)-N-acetylhomocysteine. The conjugates, Pn-Ps-A'-S-E'-B'-PRO, according to this invention, may contain spacers whose components include derivatives of, inter alia: carbon dioxide and S-carboxymethylcysteamine; carbon dioxide and S-(α-carboxyethyl)cysteamine; carbon dioxide and S-carboxymethylhomocysteamine; carbon dioxide, S-(succin-2-yl)cysteamine and glycine; carbon dioxide and S-carboxymethylcysteine.

B. Process for Making Novel Pn-Ps Intermediates and Pn-Ps-PRO Conjugates:

In disclosing this process, several stages are distinctly described:

I. Polysaccharide preparation:
a) Isolating crude pneumococcal polysaccharide, Pn-Ps;
b) Partially-hydrolyzing or mechanically-shearing the crude Pn-Ps;
c) Fractionating the partially-hydrolyzed Pn-Ps according to size and purity;

II. Conjugation:
a) Functionalizing the fractionated Pn-Ps to form the Electrophilic or Nucleophilic Reactant Pn-Ps*, preferably to exhibit about 21 reactive bromoacetyl groups per 100 Pn-Ps oligosaccharide repeating units:
b) Isolating the Immunogenic Protein (PRO), preferably the *Neisseria meningitidis* B OMPC or a subunit thereof;
c) Functionalizing the PRO to generate the Nucleophilic or Electrophilic Reactant PRO*, preferably OMPC or subunit thereof such as MIEP to exhibit reactive sulfhydryl moieties;
d) Conjugating the polysaccharide (Pn-Ps*) of step (a) with the protein (PRO*) of step (c);
e) Capping the Pn-Ps-PRO conjugate to remove residual functional groups;
f) Isolating the conjugate product.

I.a) Isolating crude pneumococcal polysaccharide, Pn-Ps:

Pneumococcal capsular polysaccharides differ chemically and antigenically due to the composition and linkage of the oligosaccharide repeating unit of the given capsular polysaccharide serotype. Isolation of the polysaccharides has to proceed along somewhat different lines depending on the physical characteristics of the given polysaccharide. However, in general, the bacteria are cultured and the Pn-Ps is recovered according to known methods [Example 3, and Williams, C. A., and Chase, M. W., *Methods in Immunology and Immunochemistry, Vol. I*, Academic Press (1967)], while the pathogens themselves are available from the ATCC. Briefly, following a large scale culture of the bacteria in appropriate nutrient media known in the art to support Pneumococcal growth, a bactericidal, such as phenol or toluene, is added to kill the organisms (Example 3).

Alcohol fractionation of the polysaccharide is then conducted in two stages. In the first stage a low alcohol concentration is used to precipitate cellular debris and other unwanted impurities, while the crude Pn-Ps remains in solution. A subsequent addition of water-miscible-alcohol to a pre-determined concentration precipitates the capsular polysaccharides while leaving additional impurities in the supernatant fluid. Resuspension in an aqueous medium is followed by removal of contaminating proteins and nucleic acids by known methods such as nuclease or proteolytic digestion or solvent extraction. The crude polysaccharide is recovered by alcohol precipitation and drying to form a powder of the crude Pn-Ps (Example 3).

I.b) Partially-hydrolyzing or mechanically-shearing the crude Pn-Ps:

Crude polysaccharide prepared essentially as described above [see also Example 3 below] has been used in an unconjugated state to formulate pneumococcal vaccines targeted for use in adults and children over 2 years of age. The process steps that follow yield a novel, partially hydrolyzed, purified Pn-Ps product having unique and defined chemical and physical properties (see Table II) useful in the preparation of conjugate vaccines. Size reduction of the crude Pn-Ps contributes to the success of subsequent purification steps to yield a highly purified Pn-Ps product. In addition, when used to prepare conjugates, the conjugation is more efficient when the new Ps-Ps of this invention is used. This is because aqueous solutions of the crude polysaccharide material are highly viscous, poorly soluble and conjugates thereof are largely-insoluble and unfilterable. The conjugation process itself is difficult to perform resulting in low yield of conjugate. In addition, removal of unconjugated Pn-Ps from the final conjugate is facilitated when the pre-conjugation Pn-Ps is of a reduced size and viscosity and improved solubility. This is significant in that the presence of free Pn-Ps in conjugate preparations makes it difficult to estimate the actual dose of conjugate Pn-Ps being administered and as it is the conjugated Pn-Ps that has the significant T-cell stimulatory effect, presence of unconjugated Pn-Ps represents a diminution of immunologically "relevant" Pn-Ps.

The dry, crude, capsular polysaccharide as prepared above may also be purified, for example, by anion-exchange chromatography or other chromatographic procedure, prior to or after partial hydrolysis, as shown in Example 6 for Pn14-Ps. The chromatographic adsorption-desorption may be used either positively or negatively. In the positive mode, the Pn-Ps is adsorbed to the resin leaving impurities in solution which are washed away prior to Pn-Ps desorption. In the negative mode, impurities are adsorbed out of the Pn-Ps solution and discarded, leaving the Pn-Ps in solution in a purified state. Alternatively, the Pn-Ps may be directly subjected to partial thermal hydrolysis, as shown in Example 4 for Pn6B-Ps or by sonic hydrolysis as shown in Example 6 for Pn14-Ps. Other hydrolytic means, such as chemical, enzymatic or physical (e.g. a high pressure cell) means are also known.

The partial-hydrolysis is accomplished by a limited thermal treatment in an aqueous medium, preferably at 50° to 110° C. for about 1 hour to about 48 hours. Alternatively, a limited high energy sonic treatment, of from 5 seconds to 5 minutes, is repeated, with periods of cooling, as many times as necessary to reach the desired viscosity or $K_d$ endpoint. The sonic hydrolysis method is preferable to thermal hydrolysis with polysaccharides having complex structures (see below). Other appropriate means known in the art to effect partial hydrolysis of polysaccharides are also applicable. For example, limited chemical hydrolysis with acid, endolytic enzyme treatment or physical shear in a blender, mill, may also be used to reduce average Pn-Ps chain size.

In a preferred embodiment, the Pn-Ps is subjected to physical shear by passage through a homogenizer at a temperature between about 0° C. and 30° C. and pressures between about 2,000 PSI and 15,000 PSI, predetermined to yield a Pn-Ps product having desirable characteristics of size, polydispersity and antigenicity (See Example 10).

A target endpoint of hydrolysis, conveniently measured by solution viscosity or high-performance size exclusion chromatography, is predetermined for each polysaccharide on a pilot scale such that antigenicity of the polysaccharide is not abrogated. As discussed above, a nominal ability to bind anti-pneumococcal type specific antibody that is no less than 70% of the binding exhibited for an equal concentration of the crude Pn-Ps starting material is considered satisfactory. This is not to say that Pn-Ps of substantially lower $M_N$, $M_W$ or number of repeating units per molecule (Table II) could not be generated by the process and that such Pn-Ps, which may fail to react above the 70% cutoff established above for the rate nephelometry assay, may be immunogenic in animals upon conjugation. This is to say that in spite of the absence of appreciable ability to bind type-specific anti-Pn-Ps antibody, low molecular weight Pn-Ps in a conjugated state may be recognized by the mammalian immune system and a good type specific anti-pneumococcal response may be generated. In this case, the term "antigenic" should be replaced by the term "immunogenic" as the operative criterion for acceptance or rejection of a given Pn-Ps preparation. In practice, however, it is most convenient to utilize the in-vitro antigenicity parameter rather than the in-vivo immunogenicity parameter as a process control.

In general, the same size reduction procedure is applicable to most polysaccharides. However, whereas the Pn6B-Ps retains it antigenicity upon extended thermal size reduction, Pn23F-Ps may lose structural integrity (removal of glycerolphostate side chains) requiring the more gentle size reduction achievable by sonic or physical shear means. Physical-shear, for example, in a Gaulin homogenizer, is a preferred method for several reasons. First, the method is amenable to scale-up. Second, the sonic- and thermal-hydrolysis methods generally require a follow-up fractionation of the hydrolyzed Pn-Ps to achieve polydispersities in the range between 1.0 and 1.5. The physical-shear method, however, generally yields Pn-Ps product having a polydispersity that falls in this range without further fractionation although fractionation may be employed to achieve additional increases in purity and decreases in CPs contamination if necessary. Third, the physical shear method may have the virtue of greater reproducibility for any given Pn-Ps as compared with thermal or sonic hydrolysis means. Fourth, the physical shear method appears to provide some advantage in the production of Pn-Ps product which retains more antigenicity for a given size than Pn-Ps of the same size produced by sonic or thermal hydrolysis.

Viscosity, which is related to average Pn-Ps molecular weight, is a convenient in-process parameter to monitor and is easily followed during hydrolysis to limit and control the degree of size reduction. Chemically and physically indistinguishable lots of Pn6B-Ps and Pn23F-Ps have been prepared simply by size reducing the polysaccharide to a consistent, target endpoint viscosity (see Table I above). Such use of in-process viscosity measurements is applicable to a wide range of crude polysaccharides, allowing for their hydrolytic size reduction without alteration of the resulting Pn-Ps's antigenic characteristics. As described above, retention of antigenicity is easily established, for example, by an Ouchterlony double-diffusion assay, rate nephelometry or other methods known in the art.

Target end-point viscosities for 1 mg/mL solutions of several Pn-Ps preparations in 0.9% sodium chloride (saline) are provided in Table III below. These values are similarly applicable to Pn-Ps derived from other pneumococcal subtypes:

TABLE III

Solution Viscosity for Crude and Hydrolyzed Pn-Ps:

| Pn-Ps Subtype | Viscosity of Crude Pn-Ps (centistokes) | Target Endpoint Viscosity (centistokes) |
| --- | --- | --- |
| Pn4-Ps | 1.8 | 1.5–1.00 |
| Pn6B-Ps | 1.4 | 1.3–1.00 |
| Pn9V-Ps | 1.4 | 1.3–1.00 |
| Pn14-Ps | 1.2 | 1.1–0.95 |
| Pn18C-Ps | 2.0 | 1.5–1.00 |
| Pn19F-Ps | 1.4 | 1.3–1.00 |
| Pn23F-Ps | 1.6 | 1.5–1.00 |

In the case of some pneumococcal polysaccharides, it is advantageous to include an additional purification step such as an ion-exchange step prior to or after partial-hydrolysis. In the case of Pn14-Ps, this step is accomplished by a batch adsorption by WHATMAN DE52 resin of anionic impurities prior to partial sonic hydrolysis. The polysaccharide being neutral at the slightly acidic pH of the treatment is recovered as the supernatant fraction in readiness for hydrolysis.

Molecular weight values for Pn6B-Ps preparations are about 900 kilodaltons (kD) before, and about 300 KD after size reduction and fractionation. For Pn23F-Ps, the respective values are about 1000 KD or more before, and about 400–500 KD after. Thus, reduction of Pn-Ps size to about 500 plus-minus about 300 kilodaltons is an appropriate target for this phase of the process for each Pn-Ps subtype.

Reprecipitation of the partially hydrolyzed material with predetermined concentrations of alcohol allows recovery and further purification of the partially-hydrolyzed Pn-Ps, as described in subsection (c) below.

I.c) Fractionating the partially-hydrolyzed Pn-Ps according to size and purity:

The polydispersity of a Pn-Ps preparation is an indication not only of the variance of subtype specific Pn-Ps chain length, it is also an indication that group-specific C-polysaccharide, as well as other contaminants, may remain in the Pn-Ps preparation. As noted above residual C-polysaccharide contamination is not useful and may even be correlated with adverse immune responses.

Selection of a narrow range of average polysaccharide molecular size (decreased polydispersity) is conveniently accomplished by differential alcohol, such as ethanol and preferably isopropanol (IPA), solubility after size reduction. The basis of this selection is that for a given Pn-Ps preparation, the alcohol solubility is inversely proportional to chain length, which in turn is proportional to molecular weight. Thus, the procedure has been applied successfully to quantitatively isolate consistently sized populations of molecules with significantly improved homogeneity over the starting size reduced Pn-Ps. In-process control of IPA fractionations is provided by performing a pilot experiment to predict the range of IPA over which the Pn-Ps precipatates. An antibody-directed Nephelose assay is employed to monitor the fractionation to ensure quantitative Pn-Ps recovery. Through this improvement, contamination by C-polysaccharide, the group-specific polysaccharide common to many different pneumococcal isolates, is reduced by from about 3 to 20 fold over the level found in crude Pn-Ps preparations. In addition, the molecular size polydispersity of the Pn-Ps preparation is concomitantly reduced to between about 1.0 and 1.4.

An alternative approach to the IPA fractionation of the size-reduced Pn-Ps is chromatography of the aqueous size reduced Pn-Ps through an appropriate size-exclusion resin, for example CL-2B resin or any other resin capable of including and fractionating polysaccharide in the 200–1000 kilodalton molecular weight range. HPSEC using a rigid size-exclusion matrix is convenient in this respect to reduce delay and increase resolution. Selection of fractions eluting from the column with a predetermined viscosity or retention time or by on-line detection yields a population of Pn-Ps molecules with the desirable characteristics of size, viscosity and purity disclosed above.

Preparation of Pn-Ps taken through the additional steps of IPA or chromatographic fractionation behave more consistently during the chemical coupling steps and therefore produce. conjugates with reproducible characteristics. Significant concomitant increases in Ps-Ps purity are also obtained, in particular, the levels of CPs are greatly diminished.

As a result of the above described manipulations and measurements, preferred characteristics for the Pn-Ps intermediates are as summarized in Table II above.

II.a) Functionalizing the fractionated Pn-Ps to form the Electrophilic or Nucleophilic Reactant Pn-Ps*, preferably to exhibit about 10–40 reactive bromoacetyl groups per 100 Pn-Ps monomer units:

The Pn-Ps from Step I.(c) above is sufficiently homogenous and has properties, such as improved solubility and reduced viscosity, to render the Pn-Ps amenable to conjugation. Many different schemes are available to those skilled in the art for preparing conjugates of polysaccharides and other moieties. The method disclosed herein is only one possible route for utilizing the novel partially hydrolyzed and fractionated Pn-Ps intermediate of this invention to form conjugates and should not be read as the exclusive mode of using the Pn-Ps intermediate.

The bigeneric spacer method disclosed by Marburg, S. et al., [U.S. Pat. No. 4,695,624; *J. Am. Chem. Soc.* 108, 5282 (1986)] is a preferred method of conjugating the fractionated and size reduced Pn-Ps to an immunogenic protein. The Pn-Ps is functionalized to display electrophilic or nucleophilic groups. The Pn-Ps* that results is then capable of reacting with a conversely functionalized protein, PRO*. The process of this invention also includes selection of a nucleophile or bis-nucleophile which will react with the activated polysaccharide to form a covalently-modified polysaccharide with pendant electrophilic sites or pendant thiol groups, thereby obviating the need to further functionalize the bis-nucleophile-modified polysaccharide prior to reacting the covalently-modified polysaccharide with the covalently-modified protein. Also, the functionalization of the protein to either moiety form may be accomplished in more than one step according to the selection of reactants in these steps.

Whatever the desired functionality of the Pn-Ps*, the size reduced, fractionated Pn-Ps has first to be solubilized in a solvent that will not interfere with the functionalization process. As it is the hydroxyl groups of the Pn-Ps that are most amenable to functionalization, removal of the Pn-Ps from water to effect the initial functionalization is critical. Replacement of acidic Pn-Ps hydrogens with a hydrophobic cation such as tetra- or tributylammonium allows the Pn-Ps to become soluble in non-aqueous solvents, such as DMSO or DMF. Naturally, there is no need to perform this replacement in Pn-Ps that are neutral (e.g. Pn14-Ps or Pn7F-Ps. Once in a nonaqueous solution, the Pn-Ps may be reacted with a bis-electrophile such as carbonyldiimidazole to form an imidazoyldiurethane. The number of functional groups per 100 Pn-Ps monomeric units is controlled at this point by addition of a limited amount of about ⅕ of the carbonyldiimidazole reagent as compared with total Pn-Ps monomers, on a molar basis, such that on average only about 10–40 out of 100 Pn-Ps monomer units is derivatized. This species is susceptible to nucleophilic substitution either by reagents such as i) cystamine dihydrochloride which permit formation of nucleophilic Pn-Ps* derivatives, or ii) 1,4-butanediamine which permit formation of electrophilic Pn-Ps* derivatives, as disclosed in U.S. Pat. No. 4,695,624 and Marburg, et al., *J. Am. Chem. Soc.*, 108, 5282 (1986).

It has recently been discovered that because some acidic pneumococcal polysaccharides, such as Pn9V-Ps, Pn4-Ps, Pn1-Ps, Pn5-Ps and *Neisseria meningitidis* B or C polysaccharides exhibit free carboxylic acid groups, as well as free hydroxyl groups, the conjugation chemistry of these polysaccharides proceeds in a slightly different fashion as compared with neutral polysaccharides or polysaccharides which are anionic by virtue of the presence of phosphodiester bonds, as in polyribosylribitolphosphate. In general, the conjugation chemistry of carboxylate-free polysaccharides proceeds by conversion of free polysaccharide hydroxyls into urethane linkages, that is, from

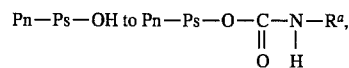

wherein $R^a$ represents the remainder of the atom-chain linking polysaccharide to protein. However, in the carboxylic acid containing polysaccharides, such as Pn-9V-Ps which contains glucuronate or Pn4-Ps which contains pyruvate groups, the chemistry proceeds from:

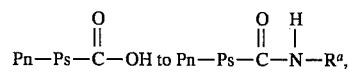

wherein $R^a$ once again represents the remainder of the atom-chain linking polysaccharide to protein. What is observed, therefore, is that the ester functionality of the urethane is either not formed in the carboxylic acid containing polysaccharide, or in addition, a simple amide bond is formed at these sites. The conjugation chemistry proceeds at a faster rate due to the presence of the carboxylic acid functionalities.

Because the carboxylic acid functionalities are thought to be important contributors to the antigenity and immunogenity of this class of anionic polysaccharides, the conjugation chemistry must be carefully controlled for these polysaccharides. The need for high polysaccharide to protein ratios in the final conjugate must be balanced against the need to retain antigenic integrity. This objective is accomplished by limiting the amount of initial carbonyldiimidazole mediated activation. Once the amide is formed, the next step involving cystamine dihydrochloride or 1,4-butane diamine may, proceed as noted above and further discussed below.

Alternatively, the carboxyl groups may be reversibly protected and then deprotected by using trimethylsilyl, or similar protecting groups which may later be removed by mild alkaline conditions, or by using 2,4-dimethoxybenzyl esters which would be acid labile. In this case, the conjugation chemistry may proceed in the conventional manner through the polysaccharide hydroxyl groups.

1. Production of Nucleophilic Pn-Ps*:

The carbonylidiimidazole activated, size reduced and fractionated Ps obtained above may be reacted, in aqueous or other solvents, with reagents such as disclosed in U.S. Pat. No. 4,695,624. A preferred reagent is cystamine dihydrochloride. Subsequent removal of excess cystamine and reduction with dithiothereitol or dithioerythreitol yields the nucleophilic sulfhydryl fuctionalized Pn-Ps. This Pn-Ps* derivative is capable of reaction with an electrophilic PRO*, for example where the protein has been modified to display pendant bromoacetyl groups.

2. Production of Electrophillic Pn-Ps*:

The carbonyldiimidazole activated, size reduced and fractionated Pn-Ps obtained above may be reacted, in aqueous or other solvents, with reagents as disclosed in the U.S. Pat. No. 4,695,624, preferably with 1,4-butanediamine (BuA$_2$). Subsequent acylation of the Pn-Ps-BuA$_2$ with p-nitrophenyl bromoacetate or similar reagent, generates the electrophilic Pn-Ps-BuA$_2$-BrAc derivative capable of reacting with a nucleophilic PRO*, such as a sulfhydryl modified protein. The degree of derivatization is measured at this point by NMR and comparison of the 1,4-butanediamine integral with a convenient monosaccharide signal such as that of the methyl of rhamnose. Preferred degrees of derivatization are between 10 to 40%, and most preferably about 20%.

II.B) Isolating the Immunogenic Protein (PRO), preferably the *Neisseria meningitidis* B OMPC, or a subunit thereof:

The protein moiety should behave as an immune enhancer. It is desirable, in the choice of protein, to avoid those that result in non-specific activation of the recipient's immune respone (reactogenicity), In U.S. Pat. No. 4,695,624, Marburg et al., used the outer membrane protein complex (OMPC) derived from *Neisseria meningitidis* to prepare polysaccharide-protein conjugates. OMPC has proven suitable in this invention, though other immunogenic proteins such as tetanus or diptheria toxoid or pertussinogen, may be used.

Various methods of purifying OMPC from the gram negative bacteria have been devised [Frasch al., *J. Exp. Med.* 140, 87 (1974): Frasch et al., *J. Exp. Med.* 147, 629 (1978); Zollinger et al., U.S. Pat. No. 4,707,543 (1987); Helting et al., *Acta Path. Microbiol. Scand.* Sect. C 89, 69 (1981); Helting et al., U.S. Pat. No. 4,271,147]. OMPC used herein was prepared as described in Example 1. In addition, a protein sununit isolated by dissociation of OMPC or by recombinant expression of material coding for an OMPC constituent protein, particularly the major membrane protein (also referred to as the mitogenic induction protein, MIP or as the major immuno-enhancing protein, MIEP) is also preferred. One method of obtaining the sununit proteins is disclosed in Example 2, 16–23 and U.S. patent application U.S. Ser. Nos. 555,978; 555,329; 555,204; and 639,457 (Merck Cases 18110, 18159 and 18160 respectively, filed on Jul. 19, 1990 and 18160IA filed on Jan. 10, 1991)

II.c) Functionalizing the PRO to generate the Nucleophilic or Electrophilic Reactant PRO*, preferably OMPC or subunit thereof to exhibit reactive sulfhydryl moieties:

The PRO isolated as in II.(b) above is next functionalized to display either electrophilic or nucleophilic groups. The PRO* that results is then capable of reacting with a conversely functionalized Pn-Ps* as prepared in II.(a) above.

1. Formation of Electrophilic PRO* Derivatives:

The isolated PRO, for example, the OMPC of Neisseria or MIEP from OMPC, is preferably reacted with a reagent such as N-(bromoacetyl)-6-aminocaproic acid p-nitrophenyl ester capable of racting with the ε-amino groups of lysine on PRO. The resultant bromoacetylated PRO, is capable of reacting with the nucleophilic deriavtives of Pn-Ps* as prepared in II.(a)1. supra.

2. Formation of Nucleophilic PRO* Derivatives:

The isolated PRO, for example, the OMPC of Neisseria or MIEP, is reacted with a reagent such as N-acetylhomocysteine thiolactone, to generate the sulfhydryl derivative of the protein. This nucleophilic derivative is capable of reaction with an electrophilic Pn-Ps* as prepared in II.(a)2 above. Typical results for this phase of the process yield sulfhydryl titers of between about 0.1 and 0.3 μmoles/mg protein.

II.d) Conjugating the polysaccharide (Pn-Ps*) of step II.(a) with the protein (PRO*) of step II.(c):

Upon formation of the reactive species Pn-Ps* and PRO* according to steps II.(a) and II.(c) supra, the conversely activated reaction partners are contacted with each other in an approximately 1:1 mass ratio. The reaction mixture should be purged of air by nitrogen, sealed and allowed to react at room temperature for about four days at between 17° and 40° C. Examples of such reactions include:

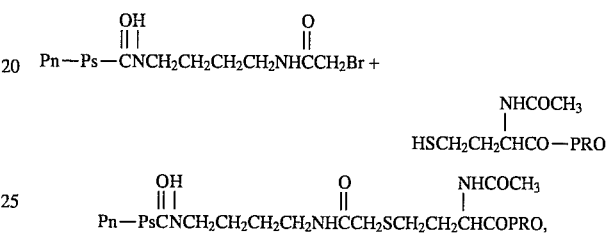

wherein an activated polysaccharide which has been reacted with 4-bromoacetamidobutylamine is reacted with a protein which has been reacted with N-acetylhomocysteinethiolactone, to form a conjugate, and:

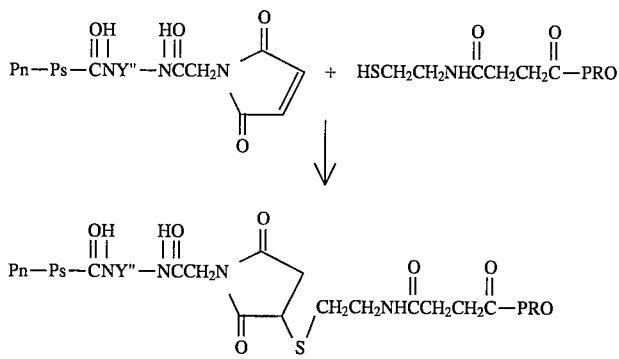

(where Y" is a $C_2$–$C_8$ alkyl radical), wherein an amino-derivatized polysaccharide which has been reacted with activated maleimido acid is reacted with a carboxy-activated protein which has been aminated with an aminothiol, to form a conjugate.

Similarly, any of the covalently-modified polysaccharides with pendant thiol groups may be reacted with the bacterial protein OMPC or MIEP having pendant electophilic centers to give a covalent conjugate. An example of such a reaction

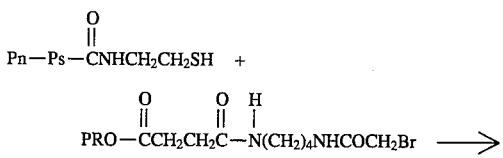

-continued

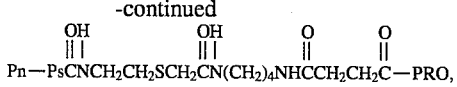

wherein an activated polysaccharide which has been reacted with an aminothiol is reacted with a corboxy-activated protein which has been reacted with monohaloacetyl derivatives of a diamine, to form a conjugate. A highly preferred linkage, according to this invention is the spacer of formula:

linkagages through the polysaccharide hydroxyls, or

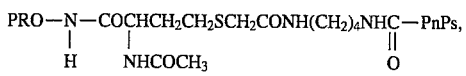

of polysaccharides bearing carboxyllic acid groups.

Should the electrophilic activity of an excess of haloacetyl groups need to be eliminated, reaction of the conjugate with a low molecular weight thiol, such as N-acetylcysteamine, will accomplish this purpose. Use of this reagent, N-acetylcysteamine also allows confirmation accounting of the haloacetyl moieties used because the S-carboxymethylcysteamine which is formed may be uniquely detected by the method of Spackman, Moore and Stein.

II.e) Capping the Pn-Ps-PRO conjugate to remove residual functional groups:

Residual electrophilic groups on either the PRO* or Pn-Ps* are quenched at the end of the reaction by addition of about a 2 to 10 fold molar excess over residual reactive groups on the conjugate of a low molecular weight nucleophile, for example, N-ethylmaleimide (NEM) to cap residual free sulfhydryls or electrophile, for example, N-acetylcysteamine to cap residual bromoacetyl moieties.

II.f) Isolating the conjugate product:

The capped product conjugate is separated from unconjugated PRO, Pn-Ps and other reactants by ultracentrifugation or diafiltration. The conjugate pellet is resuspended in an aqueous buffer wash, which may include a detergent treatment, such as 0.5% deoxycholine and salt such as 0.1M Tris pH 7–9 and about 10 mM EDTA to remove residual pyrogens and allowed to stand for between 1 and 25 hours at room temperature. The conjugate is repelleted, resuspended in aqueous buffer without detergent and then repelleted by ultracentrifugation at about 100,000×g using a fixed angle rotor for about two hours at about 1° to 20° C. or are submitted to any of a variety of other purification procedures, including difiltration gel permeation, ion exchange chromatography, gradient centrifugation or other differential adsorption chromatography, to remove non-covalently-bonded polysaccharides and proteins, using Ps, Pro, and rate nephelometry assays as well as the covalency assay for the bigeneric spacer (see below) as in vitro methods of following the desired biological activity.

The further separation of reagents may be accomplished by size-exclusion chromatography in a column or in the case of very large, non-soluble proteins, separation may be accomplished by ultracentrifugation. Resuspension of the conjugate in sterile water and ageing for about a day at 4° C. to allow complete solubilization, is followed by a low speed centriguation to remove insoluble particulates. The supernatant solution contains the final product which may be sterile filtered, formulated into vaccine compositions at immunologically effective dosage levels and sterile filled into bottles.

Analysis of the conjugate to confirm the covalency and hence the stability of the conjugate, is accomplished by hydrolyzing (preferably with 6N HCl at 110° C. for 20 hours) the conjugate, then quantitatively analyzing for the unique amino acid of the hydrolytically-stable spacer containing the thioether bond and constituent amino acids of the protein. The contribution of the amino acids of the protein may be removed, if necessary, by comparison with the appropriate amino acid standard for the protein involved, with the remaining amino acid value reflecting the covalency of the conjugate, or the amino acid of the spacer may be designed to appear outside the amino acid standard of the protein in the analysis. The convalency assay is also useful to monitor purification prodedures to mark the enhancement of concentration of the biologically active components. In the above examples, hydrolysis of

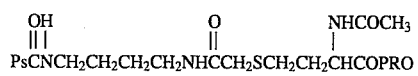

results in the release of S-carboxymethylhomocysteine,

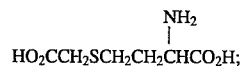

hydrolysis of

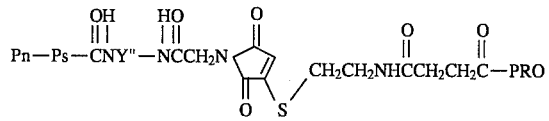

results in the release of the aminodicarboxylic acid,

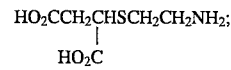

and hydrolysis of

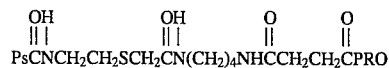

results in the release of S-carboxymethylcysteamine, $H_2NCH_2CH_2SCH_2CO_2H$ by cleavage of the Ps-A-E-S-B-PRO molecule at peptide linkages and other hydrolytically-unstable bonds. Chromatographic methods, such as those of Spackman, Moore and Stein, may then be conveniently applied and the ratio of amino acid constituents determined.

Optimal production of IgG antibody requires collaboration of B and T lymphocytes with specificity for the antigen of interest. T-lymphocytes are incapable of recognizing polysaccharides but can provide help for anti-polysaccharide IgG antibody responses if the polysaccharide is covalently linked to a protein which the T cell is capable of recognizing.

C. Vaccine Formulations and Utility:

In a preferred embodiment, the conjugate product is adsorbed onto aluminum hydroxide gel. This is accomplished, for example, by preparation of a conjugate stock solution equivalent to a concentration of 20 μg/ml of Pn-Ps. Portions may be diluted 1:1, 1:5, and 1:10 with sterile water. Portions of each of these samples, including a portion of the 20 μg/ml stock, are diluted 1:1 with an aluminum hydroxide diluent containing 0.85 mg/ml $Al^{+3}$, 1.7% NaCl (w/v) and 100 μg/mL thimerosol. The solution pH is adjusted to about 7.5 with 1N NaOH resulting in solutions having a Pn-Ps concentration of 10, 5, 2, and 1 μg/mL. Doses of between about 0.1 mL and 0.75 mL of each of these formulations are appropriate for administration to different age and weight range recipients. The vaccine formulated as described has been found to raise significant, subtype-specific, anti-pneumococcal polysaccharide immune responses in 2–3 month old infant monkeys for Pn6B-Ps-OMPC, Pn14-Ps-OMPC, Pn19F-Ps-OMPC and Pn23F-Ps-OMPC. The Pn-Ps-OMPC conjugate vaccine has, in addition, been found to be T-cell dependent in athymic mice.

It should be clear from this disclosure that other polysaccharides having properties as defined herein and processes for making the Ps having those properties, will have useful application in the preparation of conjugates other than those comprising partially hydrolyzed and fractionated pneumococcal polysaccharides. These conjugates could then be used to prevent diseases caused by other pathogenic organisms. For example, the group B streptococci, a cause of neonatal meningitis, *Neisseria meningitidis* B or C, a cause of infantile meningitis, or *E. coli,* an important cause of urinary tract and other opportunistic infections, could be used as polysaccharide sources. These polysaccharides, as well as the Pn-Ps and covalent conjugates thereof may also provide important components for combination vaccine formulations. Such combinations may, for example, include immunologically effective amounts of adjuvant, such as Freunds, Ribi or immunomodulatory compounds, such as the interleukins, interferons (see, for example, compounds listed in: *Market Letter,* Nov. 30, 1987, p. 26–27; *Genetic Engineering News,* Jan. 1988, Vol. 8, p.23) or additional immunogens. In a preferred embodiment, a composition comprising immunologically effective amounts of the conjugate of this invention is included with one or more of the vaccines against hepatitis B, hepatitis A, non-A non-B hepatitis, AIDS, diptheria, pertussis, tetanus, measels, mumps, rubella, varicella, polio, or *Haemophilus influenzae* b. Preferred additional vaccines, selected from those just mentioned, are selected from among PevaxHIB®, Recombivax HB®, M-M-R® and a trivalent DTP vaccine.

The following examples are provided to further disclose the invention and should not be read as limiting on the invention.

EXAMPLE 1

Preparation of *Neisseria meningitidis* B11 Serotype 2 OMPC

A. Fermentation

1. *Neisseria meningitidis* Group B11

A tube containing the lyophilized culture of *Neisseria meningitidis* [obtained from Dr. M. Artenstein, Walter Reed Army Institute of Research (WRAIR), Washington, D.C.] was opened and Eugonbroth (BBL) was added. The culture was streaked onto Mueller Hinton agar slants and incubated at 37° C. with 5% $CO_2$ for 36 hours, at which time the growth was harvested into 10% skim milk medium (Difco), and aliquots were frozen at −70° C. The identity of the organism was confirmed by agglutination with specific antiserum supplied by WRAIR and typing serum supplied by Difco.

A vial of the culture from the second passage was thawed and streaked onto 10 Columbia Sheep Blood agar plates (CBAB-BBL). The plates were incubated at 37° C. with 5% $CO_2$ for 18 hours after which time the growth was harvested into 100 mL of 10% skim milk medium, aliquots were taken in 0.5 mL amounts and frozen at −70° C. The organism was positively identified by agglutination with specific antiserum, sugar fermentation and gram stain.

A vial of the culture from this passage was thawed, diluted with Mueller-Hinton Broth and streaked onto 40 Mueller-Hinton agar plates. The plates were incubated at 37° C. with 6% $CO_2$ for 18 hours after which time the growth harvested into 17 mL of 10% skim milk medium, aliquotted in 0.3 mL amounts and frozen at −70° C. The organism was positively identified by Gram stain, agglutination with specific antiserum and oxidase test.

2. Fermentation and collection of cell paste a. Inoculum Development—The inoculum was grown from one frozen vial of *Neisseria meningitidis* Group B, B-11 from above (passage 4). Ten Mueller-Hinton agar slants were inoculated and six were harvested approximately 18 hours later and used as an inoculum for 3×250 mL flasks of Gotschlich's yeast dialysate medium at pH 6.35. The $OD_{660}$ was adjusted to 0.18 and incubated until the $OD_{660}$ was between 1 and 1.8. 1 mL of this culture was used to inoculate each of 5×2L, Erlenmeyer flasks (each containing 1 liter of medium; see below) and incubated at 37° C. in a shaker at 200 rpm. The O.D. was monitored at hourly intervals following inoculation. 4 liters of broth culture, at an $OD_{660}$ of 1.28 resulted.

70 Liter Seed Fermenter—Approximately 4 liters of seed culture was used to inoculate a sterile 70-liter fermenter containing about 40 liters of complete production medium (see below). The conditions for the 70-liter fermentation included 37° C., 185 rpm with 10 liters/minute air sparging and constant pH control at about pH 7.0 for about 2 hours. For this batch, the final $OD_{660}$ was 0.732 after 2 hours.

800-Liter Production Fermenter

Approximately 40 liters of seed culture were used to inoculate a sterile 800 liter fermenter containing 568.2 liters of complete production medium (see below). The batch was incubated at 37° C., 100 rpm with 60 liters/minute air sparging and constant pH control at pH 7.0. For this batch, the final OD was 5.58 thirteen hours after inoculation.

3. Complete Medium for Erlenmeyer flasks and 70-and 800-liter fermenters

| Fraction A | |
|---|---|
| L-glutamic acid | 1.5 g/liter |
| NaCl | 6.0 g/liter |
| $Na_2HPO_4$.anhydrous | 2.5 g/liter |
| $NH_4Cl$ | 1.25 g/liter |
| KCl | 0.09 g/liter |
| L-cysteine HCl | 0.02 g/liter |

Fraction B (Gotschlich's Yeast Dialysate):

1280 g of Difco Yeast Extract was dissolved in 6.4 liters of distilled water. The solution was dialyzed in 2 Amicon DC-30 hollow fiber dialysis units with three H10SM cartridges. 384 g $MgSO_4 \cdot 7\text{-}H_2O$ and 3200 g dextrose were dissolved in the dialysate and the total volume brought to 15 liters with distilled water. The pH was adjusted to 7.4 with NaOH, sterilized by passage through a 0.22μ filter, and transferred to the fermenter containing Fraction A.

For the Erlenmeyer flasks: 1 liter of Fraction A and 25 mL of Fraction B were added and the pH was adjusted to 7.0–7.2 with NaOH.

For the 70 liter fermenter: 41.8 liters of Fraction A and 900 mL of Fraction B were added and the pH was adjusted to 7.0–7.2 with NaOH.

For the 800 liter fermenter: 553 liters of Fraction A and 15.0 liters of Fraction B were added and the pH was adjusted to 7.1–7.2 with NaOH.

b. Harvest and Inactivation After the fermentation was completed, phenol was added in a separate vessel, to which the cell broth was then transferred, yielding a final phenol concentration of about 0.5%. The material was held at room temperature with gentle stirring until the culture was no longer viable (about 24 hours).

c. Centrifugation

After about 24 hours at 4° C., the 614.4 liters of inactivated culture fluid was centrifuged through Sharples continuous flow centrifuges. The weight of the cell paste after phenol treatment was 3.875 kg. Alternately the phenol killed fermentation broth was harvested by dialfiltration as described below.

B. OMPC Isolation

Step 1. Concentration and diafiltration

The phenol inactivated culture was concentrated to about 30 liters and diafiltered in sterile distilled water using 0.2-μm hollow fiber filters (ENKA).

Step 2. Extraction

An equal volume of 2X TED buffer [0.1M TRIS 0.01M EDTA Buffer, pH 8.5, with 0.5% sodium deoxycholate] was added to the concentrated diafiltered cells. The suspension was transferred to a temperature regulated tank for OMPC extraction at 56° C. with agitation for 30 minutes.

The extract was centrifuged at about 18,000 rpm in a Sharples continuous flow centrifuge at a flow rate of about 80 mL/minute, at about 4° C. The viscous supernatant fluid was then collected and stored at 4° C. The extracted cell pellets were reextracted in TED buffer as described above. The supernatant fluids were pooled and stored at 4° C.

Step 3. Concentration by Ultrafiltration

The pooled extract was transferred to a temperature regulated vessel attached to AG-Tech 0.1-μm polysulfone filters. The temperature of the extract was held at 25° C. in the vessel throughout the concentration process. The sample was concentrated tenfold at an average transmembrane pressure of between 11 and 24 psi.

Step 4. Collection and Washing of the OMPC

The retentate from Step 3 was centrifuged at about 160,000×g (35,000 rpm) at about 70° C. in a continuous flow centrifuge at a flow rate between 300 to 500 mL/minute, and the supernatant fluid was discarded.

The OMPC pellet was suspended in TED Buffer (190 mL buffer; 20 mL/g pellet) Step 2 and Step 4 were repeated twice (skipping Step 3).

Step 5. Recovery of OMPC Product

The washed pellets from Step 4 were suspended in 100 mL distilled water with a glass rod and a Dounce homogenizer to insure complete suspension. The aqueous OMPC suspension was then filter sterilized by passage through a 0.22-μm filter and the TED buffer was replaced with water by diafiltration against sterile distilled water using a 0.1-μm hollow fiber filter.

EXAMPLE 2

Purification of a Subunit of OPMC: Preparation of Purified MIEP from OMPC or From Recombinant Cells by Polyacrylamide Gel Electrophoresis Acrylamide/BIS (37.5:1) gels, 18×14 cm, 3 mm thick were used. The stacking gel was 4% polyacrylamide and the separating gel was 12% polyacrylamide. Approximately 5 μg of OMPC protein or recombinant host cell protein was used per gel. To 1 mL of OMPC was added 0.5 mL of sample buffer (4% glycerol, 300 mM DTT, 100 mM TRIS, 0.001% Bromophenol blue, pH 7.0). The mixture was heated to 105° C. for 20 minutes and allowed to cool to room temperature before loading onto the gel. The gel was run at 200–400 milliamps, with cooling, until the Bromophenol blue reached the bottom of the gel. A vertical strip of the gel was cut out (about 1–2 cm wide) and stained with Coomassie/ cupric acetate (0.1%). The strip was destained until the MIEP band (about 38 KD) became visible. The strip was then placed into its original gel position and the MIEP area was excised from the remainder of the gel using a scalpel.

The excised area was cut into cubes (about 5 mm) and eluted with 0.01M TRIS-buffer, pH 8.1. After 2 cycles of elution the eluate was evaluated for purity by SDS-PAGE. The eluate was combined with a common pool of eluates and dialyzed for 48 hours against 60 mM ammonia-formic acid, pH 10. Alternatively, the eluted protein can be dialyzed against 50% acetic acid in water. After dialysis the eluted protein was evaporated to dryness. The material was further purified by passage through a PD10 sizing column (Pharmacia, Piscataway, N.J.), and was stored at room temperature.

EXAMPLE 3

Culturing Streptococcus pneumoniae subtypes and Isolation of Crude Pn-Ps:

I. Culturing Pneumococci:

Methods of culturing pneumococci are well known in the art [Chase, M. W., *Methods of Immunology and Immunochemistry* 1, 52 (1967)]. Isolates of pneumococcal subtypes are available from the ATCC. The bacteria are identified as encapsulated, non-motile, Gram-positive, lancet-shaped diplococci that are alpha-hemolytic on blood-agar. Subtypes are differentiated on the basis of Quelling reaction using specific antisera. Master and stock seed cultures are preferably maintained lyophilized or below 8° C. In a preferred culture methods, stock cultures are restored with Heart Infusion Broth, plated onto Heart Infusion Agar, containing 10% defibrinated rabbit blood and incubated at 37° C.±2° C. for approximately 18 hours.

The growth on the plate is resuspended in Heart Infusion Broth and an aliquot of the resuspended growth is used to inoculate 100 ml of Heart Infusion Broth containing 10% defibrinated rabbit blood, which is incubated as a stationary culture for approximately 18 hours at 37° C.±2° C. The 100 ml of liquified culture (working seed) is checked for purity by microscopic examination of a Gram-stained smear and growth on Heart Infusion Blood Agar plates. The working seed may be stored at 2°–8° C. for up to 14 days or used immediately. Two-liter Erlenmeyer flasks or other suitable vessels, containing Pneumococcus Inoculum Medium (YUF), containing dextrose (25 gm/liter), are inoculated with working seed and incubated stationary for approximately 8–24 hours at 37° C.±2° C. The incubation period varies as specified depending on the type of *Streptococcus pneumoniae* being grown. The pH of the fermentation is adjusted to maintain a target pH range of 6.0 to 7.2 by the periodic addition of 12% sodium bicarbonate solution until an optical density of 1.5 to 4.0 is reached. Optical density is monitored at 660 nanometers. A sample of the growth is examined microscopically and a serological agglutination reaction is performed to check purity. The growth from this stage is transferred into a seed fermenter containing 40 liters of Pneumococcus fermenter Medium composed of distilled water, a dry charge of the components for Pneumococcus seed medium (YUF), Yeast Extract Ultrafiltrate, UCON, and dextrose (approximately 25 gm/liter). The culture is incubated at 37° C.±2° C. with mild agitation for approximately 2–12 hours. The pH is controlled to 6.0 to 7.2 by the periodic addition of sodium hydroxide solution. A fermenter containing 525 liters of Pneumococcus fermenter Medium, composed of distilled water, a dry charge of the components for Pneumococcus Production Medium (YUF), Yeast Extract Ultrafiltrate, UCON and dextrose (approximately 25 gm/liter), is inoculated with approximately 50 liters of one 2–12 hour seed culture. The culture is incubated at 37° C.±2° C. with mild agitation for 6–30 hours depending on which type is being grown. The pH is controlled at 6.0 to 7.2 by periodic additions of sodium hydroxide solution. The fermentation is followed by optical density determination, and the fermentation is terminated when the dextrose is completely utilized as indicated by no further changes in pH.

The pathogenic organisms are killed immediately after fermentation is terminated. This is accomplished by addition of phenol to a concentration of about 1% and the kill allowed to proceed for 2–12 hours at ambient temperature.

II) Isolating Crude Pn-Ps:

Denatured alcohol is added to the killed culture in a sufficient quantity to precipitate cell debris and nucleic acids, which is removed by centrifugation. The crude polysaccharide is then precipitated from the supernatant fluid by addition of more denatured ethanol. The solids are collected by centrifugation and the supernatant fluid discarded.

Nucleic acid contamination is reduced by solubilization of the polysaccharide in a neutral aqueous solution such as 1–5% sodium acetate, or 0.05M phosphate buffer to which is added nuclease and about 0.01M magnesium chloride. After about 60–120 minutes at about 36° C., the pH is adjusted to about 8.0 and a protease such as trypsin, is added to digest proteinaceous contaminants.

Additional impurities may be eliminated by reprecipitation of the polysaccharide in sodium acetate with denatured alcohol or isopropanol, followed by resolubilization in distilled water. Addition of cetrimonium bromide at about 8° C. precipitates impurities which are removed by centrifugation. Addition of sodium acetate and an aliquot of denatured alcohol or isopropanol allows removal of additional impurities. The polysaccharide is recovered by addition or more alcohol and centrifugation. The precipitate is washed with absolute ethanol until a white powder is obtained. The polysaccharide is collected by filtration, washed with absolute ethanol and acetone and dried under vacuum to yield the crude Pn-Ps as a powder.

EXAMPLE 4

Preparation of Partially-Hydrolyzed Purified Pn6B-Ps:

(1) Thermal Hydrolysis: A 3.0 g portion of crude Pn6N-Ps powder was solubilized in 1200 mL saline (0.9% NaCl) with stirring at room temperature for about 4 hours and stored at 4° C. overnight. The solution was then hydrolyzed in a cold-finger reflux condenser apparatus at 100° C. for 24 hours and cooled to room temperature. Sodium acetate reagent (59.7 g) was added to a final concentration of 3% (w/v).

(2) Serological Probe: An isopropanol (IPA) fractionation pilot study and antibody-directed end-point Nephelose assay, performed on a 10 mL portion of the sample, showed that the Pn6B-Ps would precipitate at 40–50% IPA.

(3) First IPA Addition: The hydrolyzed sample (volume—1210 mL, from step 1 above) was brought to 43.5% IPA by the addition of 932 mL IPA (added dropwise with stirring at room temperature). The sample was allowed to stir for 15–30 minutes and then centrifuged at 11,000×g for 30 minutes (Beckman JA-10 rotor; 8,000 rpm; 20° C.). The waste pellet was triturated with absolute EtOH in a 250-mL Omnimix jar, then collected on a 60-mL sinter glass funnel. The precipitate was washed directly on the funnel with absolute EtOH, then acetone and dried in vacuo over $CaCl_2$ at room temperature in preparation for analysis.

(4) Second IPA Addition and Product Recovery: The 43.5% IPA supernatant fluid [volume=2020 mL, from step 3 above] was brought to 46.0% IPA by adding 93.5 mL IPA dropwise while stirring at room temperature The sample was aged and centrifuged as in step 3 above. The pellet was triturated, collected, washed and dried as in step 3 above. The Pn6B-Ps produce weighted 1,650 mg, and it had a $K_d$ of 0.62 and a phosphorus content of 3.3%

EXAMPLE 5

S. pneumoniae 6B-OMPC Conjugate, Pn6B-Ps-OMPC:

A. Preparation of Dowex 50×2 tetrabutylammonium Resin [Dowex 50 ($Bu_4N^+$)]:

Dowex 50×2 (200–400 mesh) $H^+$ form, (72 g) was slurried in water, charged to a column and washed sequentially with water, 6N HCl and then water until the effluent tested neutral to pH paper. A 10% aqueous solution of tetrabutylammonium hydroxide was then run through the column until the effluent tested strongly alkaline. Finally, water was run through the column until the effluent again tested neutral.

B. Pn6B(Bu4N+):

Pn6B-Ps (600 mg), size reduced and fractionated (see Table I Pn6B-Ps lot 1 for physical properties) was dissolved in sterile distilled water (60 mL) and the solution magnetically stirred until all solids went into solution (1.5 h). The polysaccharide solution was applied to the rinsed resin and allowed to pass through the bed by gravity (4.5 h). The column was washed with water (10–12 mL) and the combined effluents lyophilized, providing 640 mg of dry Pn6B-Ps tetra-n-butyl ammonium salt, Pn6B(n-Bu4N+).

C. Pn6B-$BuA_2$:

Pn6B(n-$Bu_4N^+$)(640 mg) was dissolved in dimethylsulfoxide (DMSO) (24 mL) and magnetically stirred for 30 min, at which time all solids appeared to be in solution. To this mixture was added 1, 1'-carbonyldiimidazole (44.2 mg) and the reaction stirred at room temperature (60 min). In a separate flask, a solution of butanediamine dihydrochloride ($BuA_2$·2HCl, 1.022 g) in water (16 mL) was made basic (pH 10.2) by the addition of 10N NaOH. The solution was filtered through a 0.2 μm sterile filter, and cooled in an ice bath. The aged DMSO mixture containing the activated polysaccharide was added to the cold $BuA_2$·2HCl solution, in a slow steady stream and the resulting solution stirred at 0° C. (15 min). The reaction mixture was allowed to warm up to room temperature and stirred for an additional 1 h, after which it was transferred to dialysis tubing and dialyzed (4° C.) against the following: 1] 15 L of 0.1M pH 7.0 sodium phosphate buffer for 6 hr; 2] 15 L 0.01M pH 7.0 sodium phosphate buffer, 12 hr; 3] 15 L 0.01M pH 7.0 sodium phosphate buffer, 9 hr; 4] 15 L distilled H₂O, 17.5 hr. The contents of the dialysis tubing was lyophilized, providing 222 mg of Pn6B-1,4-butane diamine (Pn6B-BuA$_2$). The NMR (300 MHz, D₂O) of about 5 mg of this material revealed a loading of 22 diamine residues per 100 Pn6B-Ps repeating monomer units, by comparing the integrals of the resonances of the butane diamine methylenes and the rhamnose methyl protons of Pn6B-Ps.

Pn6B-BuA$_2$-BrAc:

Pn6B-BuA$_2$ (210 mg) was dissolved in pH 9.04, 0.1M Kolthoff borate-phosphate buffer (21 mL) and the mixture magnetically stirred for 30 min to effect solution. To this aqueous solution was added a mixture consisting of p-nitrophenyl bromoacetate (210 mg) in acetonitrile (2.6 mL) and the reaction stirred overnight (20 hr, 4° C.). The solution was transferred to dialysis tubing and dialyzed (4° C.) against the following: 1] 15 L sterile distilled H₂O, 12.3 hr; 2]15 L sterile distilled H₂O, 8.25 hr; 3] 15 L sterile distilled water, 5.5 hr. From the contents of the bag, 1.7 ml was removed for assays (NMR and HPSEC-universal calibration or molecular size analysis) and then 0.449 g of dried pH 8 phosphate buffer salt (prepared by lyophilizing a 0.1M, pH 8 sodium phosphate solution) was added. After complete dissolution (30 min.), the solution was filtered through a sterile 0.2 μm filter, yielding a pH 8 solution of Pn6B-BuA$_2$-BrAc.

Pn6B-OMPC:

Sterile OMPC (40 mL, 4.5 mg/ml) was pelleted by ultracentrifugation (4° C., 43K rpm, 2 hr) in four 10 ml centrifuge tubes. Each pellet was resuspended in 3 mL of a sterile-filtered (0.22 μm) thiolation mixture which consisted of the following: N-acetylhomocysteine thiolactone hydrochloride (164 mg), ethylene-diamine-tetraacetic acid disodium salt (255 mg) and dithiothreitol (53 mg) in pH 11.09, Na₂B₄O₇ buffer (30 mL). The resuspended pellets were homogenized (Dounce), combined, the vessel degassed and blanketed with nitrogen and aged overnight (19 hr) at room temperature. The solution was divided among three ultracentrifuge tubes, topped with 1M KH₂PO₄ and the protein pelleted (4° C., 43K rpm, 2 h). The pellets were resuspended in 0.1M sodium phosphate, pH 8 buffer (30 mL), homogenized (Dounce) and repelleted (4° C., 43K rpm, 2 h). The sterile protein pellet was used resuspended in the filtered Pn6B-BuA$_2$-BrAc solution. An Ellman's test was performed immediately, and showed an SH titer of 34 μmol. The reaction mixture was degassed, blanketed with nitrogen and aged for 91 hr. at room temperature.

The protein was capped by the addition of 1 mL of a (0.22 μm sterile filter) solution consisting of the following: N-ethylmaleimide (75 mg) in 5 mL pH 8.0 0.1M sodium phosphate buffer. This mixture was aged for 4 hr at room temperature, following which, 300 μL of N-acetyl cysteamine (0.22 μm sterile filtered) was added and the solution aged for an additional 19.5 hr.

The sterile capped conjugate was divided among four centrifuge tubes, topped with 0.1M, pH 7 sodium phosphate buffer, and pelleted by ultracentrifugation (4° C., 43K rpm, 2 h), then resuspended and homogenized (Dounce) in sterile pH 7, 0.1M NaPO₄ buffer (42 mL). Following recentrifugation as before, the pellets were resuspended in a Pounce homogenizer in a total of 50 mL of sterile distilled water. After ageing for 17 hr at 4° C., the conjugate preparation was centrifuged at 1000 rpm for 3.5 minutes in a TH 4 rotor in a TJ-6 centrifuge and a small amount of sediment removed. The final product conjugate suspension was assayed for protein (Lowry), Pn6B-polysaccharide (phenol/sulfuric acid), unconjugated polysaccharide (size exclusion chromatography—rate Nephelometry) and amino acids (amino acid analysis). The results were as follows:

| | |
|---|---|
| Pn6B-Polysaccharide | 0.33 mg/ml |
| Protein | 2.2 mg/ml |
| Pn6B-Ps/OMPC | 0.15 |
| Free Pn6B-Ps | <5 area % |
| S-carboxymethylhomocysteine/lysine | 7.7% |
| S-carboxymethylcysteamine/lysine | 1.6% |

EXAMPLE 6

Preparation of Partially-Hydrolyzed, Purified Pn14-Ps:

(1) Treatment with Anion-Exchange Resin: A 2.81 gram portion of Pn14-Ps powder was solubilized in 1124 mL distilled H₂O with stirring at room temperature for about 4 hours and then stored at 4° C. overnight. The solution was added to 60 grams of DE52 (Whatman, diethylamino-ethyl cellulose) which had been preswollen for ca. 15 hrs. in distilled H₂O at pH ca. 5–6. The slurry was gently shaken on a platform shaker at room temperature for ca. 15 hrs, after which it was centrifuged in a Beckman JA-10 rotor at 5,000 rpm for 15 min. at 20° C. The supernatant fluid was further clarified through a sinter glass funnel (150 ml, medium porosity) and collected into a 2L side arm flask.

(2) Sonic Hydrolysis: The DE52-treated Pn14-Ps (volume—1100 mL, from step 1 above) was sonicated in a plastic beaker on an ice bath with a Branson Sonifier (one-half inch probe, setting 8) for 2 min. The sample was allowed to cool for ca. 15 min. while the viscosity was determined and then was sonicated for additional 1 min. intervals. A viscosity end point of 1.096 centistokes was reached after the last sonic treatment. The hydrolyzed sample was brought to room temperature and sodium acetate reagent (18.0 g) was added to a final concentration of 1% (w/v).

(3) Serologic Probe: An isopropanol (IPA) fractionation pilot study and antibody-directed end-point Nephelose assay, performed on a 10 mL portion of the sample, showed that the Pn14-Ps would precipitate between 35–45% IPA.

(4) First IPA Addition: The hyrolyzed sample [volume—1090 mL, from step 2 above] was brought to 39.3% IPA by the addition of 706 mL IPA (added dropwise with stirring at room temperature). The sample was allowed to stir for 15–30 minutes and then centrifuged at 11,000×g for 30 minutes (Beckman JA-10 rotor; 8,000 rpm; 20° C.) and the supernatant fluid decanted. The waste pellet was triturated with absolute EtOH in a 250-mL Omnimix jar, then collected on a 60-mL sinter glass funnel. The precipitate was washed directly on the funnel with absolute EtOH, then acetone, and dried in vacuo over CaCl₂ at room temperature in preparation for analysis.

(5) Second IPA Addition and Product Recovery: The 39.3% IPA supernatant fluid [volume—1712 mL, from step 4 above] was brought to 41.8% IPA by adding 73.5 mL IPA dropwise while stirring at room temperature. The sample was aged and centrifuged as in step 4 above. The pellet was triturated, collected, washed and dried as in step 4 above. The Pn14-Ps product weighted 1,399 mg.

(6) Dialysis and Lyophilization: A portion (1385.6 mg) of the sample from Step 5 above, was solubilized in 554 mL of distilled H₂O at room temperature for 2–3 hours. The solution (2.5 mg/mL) was transferred to dialysis tubing (12,000 MW cutoff; 45 mm) and dialyzed vs. distilled H₂O for 27 hours with 2 additional changes of distilled H₂O.

Then the dialyzed sample was transferred to lyophilization flasks, shell-frozen in a dry ice:methanol bath and lyophilized on a Virtis (Freezemobile) lyophilizer for 2-½ days until dry. The recovery of the final Pn14-Ps product was 1326.8 mg, which had a $K_d$ of 0.56.

From this disclosure it should be obvious to those skilled in the art that other neutral Pn-Ps subtypes, such as Pn7F-Ps, could be prepared according to the method disclosed here, and conjugated as for Pn14-Ps which is also a neutral polysaccharide.

EXAMPLE 7

Conjugation of Outer Membrane Protein Complex with Pneumococcal 14 Polysaccharide, Pn14-Ps-OMPC:

a. Preparation of the 1,4-butanediamine derivative of Pn14-Ps ((14-BuA2):

A 410 mg portion of Pn14-Ps after storage in vacuo over $P_2O_5$ for 3 hr., was covered with 26 mL of dimethylsulfoxide (DMSO) and stirred for 0.75 hr. to dissolve. To this was added 62 mg of carbonyl diimidazole and the resultant solution stirred at room temperature (r.t.) for 80 min.

A solution containing 1.067 g of 1,4-butanediamine dihydrochloride ($BuA_2 \cdot 2HCl$) in 38.5 mL of $H_2O$ was prepared and its pH adjusted to 10.20 with 2.5N NaOH. This solution was filtered through a Millex 0.2 μm GV filter and cooled in an ice bath.

The aged DMSO solution was added to the cold $BuA_2$ solution and stirred an additional 10 min. in the ice bath. It was then aged at r.t. for 50 min., after which the solution was charged to two 12" lengths of Spectrapot 2 dialysis tubing, clipped off 1 cm from the top of the liquid and dialyzed vs: 1) 15 L of pH 7.0, 0.1M sodium phosphate buffer for 16.5 hr. 2) 15 L of pH 7.0, 0.1M sodium phosphate buffer for 8 hr; 3) 15 L of pH 7.0, 0.1M sodium phosphate buffer for 8 hr; 4) 15 L of $H_2O$ for 17.5 hr. It was then lyophilized to yield 210 mg of the 1.4-butane diamine derivative of Pn14-Ps ($Pn14-BuA_2$). An NMR spectrum of a ca. 5 mg sample showed a "loading" of approximately 31 butanediamine residues per 100 repeating units of polysaccharide defined by comparing the integrals of the butanediamine methylenes and the N-acetyl methyl (of Pn14-Ps) resonances.

b. Preparation of the bromoacetylated butanediamine derivative of Pn14-Ps ($Pn14-BuA_2-BrAc$):

$Pn14-BuA_2$ (210 mg) was covered with 36 mL of a 0.1M, pH 9.0 borate-phosphate buffer and stirred for 2.5 hr. to effect solution, Then, 195 mg p-nitrophenyl bromoacetate dissolved in 4 mL of acetonitrile was added. The resulting mixture was stirred 21 hr at 4° C. It was then dialyzed in Spectrapot 2 tubing vs: 1) 15 L distilled $H_2O$ for 6 hr, 2) 15 L of distilled $H_2O$ for 14.5 hr and 3) 15 L of $H_2O$ for 6 hr. From the dialyzed contents of the bag, 2.0 mL were removed for assays and then 492 mg of dried pH 8.0 phosphate buffer salt (prepared by lyophilizing a 0.1M sodium phosphate, pH 8.0 solution) was added. Solution was filtered through two 0.2 μm Corning filters resulting in an aqueous pH 8.0 solution of Pn14-BuA2-BrAc (43 mL).

c. Conjugation of OMPC to $Pn14-BuA_2-BrAc-Ps$:

Fifty mL of OMPC (concentration 3.2 mg/mL) was charged to five 10-mL centrifuge tubes and centrifuged in a Beckman 80 Ti rotor at 43,000 rpm (43K), at 4° C. for 2 hr. A thiolation mixture was prepared by dissolving 350 mg of EDTA (ethylene diamine tetracetic acid disodium salt) and 64 mg of dithiothreitol (DTT) in 30 mL of $Na_2B_4O_7$ buffer, pH 11.0. 346 mg of N-acetyl homocysteine thiolactone was added and the solution filtered through a 0.2-μm Corning filter (cup type).

The pellets from the above centrifugation were each dislodged with 3 mL of the filtered thiolation mixture (15 mL total), transferred to a Dounce homogenizer and resuspended. The tubes were rinsed by serial transfer of an additional 5 mL of the thiolation solution. The rinsing process was repeated with an additional 5 mL of thiolatin solution. The combined rinses were homogenized in the Dounce and the total resuspended material (25 mL) was transferred to a 100-mL round-bottom flask.

After sealing with a septum and replacing the air with $N_2$ using a Firestone valve, the reaction mixture was aged for 21 hr. The 25 mL reaction mixture was then divided among three centrifuge tubes, each of which was topped with 1M $KH_2PO_4$ (aqueous) and then centrifuged for 2 hr at 43K rpm and 4° C. The supernatant fluids were removed and the pellets resuspended in 0.1M sodium phosphate pH 8.0 buffer (a total of 30 mL was the final resuspension volume).

A second ultracentrifugatin (2 hr, 4° C., 43K rpm) was then performed. After removing the supernatant fluid, the pellets were resuspended by the Dounce method in the filtered $Pn14-BuA_2-BrAc$ solution prepared above. An Ellman assay at this point indicated a total of about 23 μmoles of thiol.

It should be noted that the filtration of the $Pn14-BuA_2-BrAc$ solution occurs just prior to the resuspension of the thiolated protein. The resultant reaction (i.e., Pn $14-BuA_2$-BrAc with thiolated OMPC) was aged under $N_2$ (with degassing) in a $N_2$ box at r.t. for 114 hr.

The reaction was then capped (i.e., the reactive moieties on the Pn14-Ps and OMPC are deactivated) as follows: A solution containing 75 mg N-ethylmaleimide (NEM) in 5 mL of pH 8.0, 0.1M sodium phosphate buffer) was added and the mixture aged for an additional 22.5 hr. The capped reaction mixture (35 mL) was divided among 4 centrifuge tubes and centrifuged (43K, 2 hr., 4° C.). The pellets were resuspended in 40 mL TED buffer (0.1M Tris, o.01M EDTA, 0.5% DOC, pH 8.5) and aged at room temperature for 19 hrs. The solution was then centrifuged (43K, 2 hr., 4° C.). The pellets were resuspended in 40 mL 0.1M pH 8 sodium phosphate buffer, and then recentrifuged (43K, 2 hr., 4° C.). These pellets were resuspended in 44 mL of $H_2O$ and aged at 4° C. for 17 hrs. A low speed centrifugation (1000 rpm, 3.5 min.) afforded a small pellet which was discarded. The supernatant fluid was removed, resulting in 43 mL of bulk conjugate, having the following analytical characteristics:

| Test | Results |
| --- | --- |
| a. Ps Content | 387 mcg/mL |
| b. Protein | 1300 mcg/mL |
| Ps/Protein ratio (Calc.) | 0.30 |
| c. Free Ps | <5 area % |
| d. Amino Acid Analysis | |
| SCMHC/lysine | 9.8% |
| SCMC/lysine | 3.5% |

EXAMPLE 8

Preparation of the Pn23F-Ps Intermediate:

(1) Sonic Hydrolysis: A 3.0-g portion of Pn 23F Ps powder was solubilized in 1200 mL saline (0.9% NaCl) with stirring at room temperature for about 4 hours. The solution was then sonicated in a plastic beaker in an ice bath with a Branson Sonifier (one-half inch probe, setting 8) for intervals of 3 minutes, up to 15 min. total. The viscosity was checked after each interval. After 15 min., another 5 min. sonication was performed to obtain a viscosity endpoint of 1.206 centistokes. The hydrolyzed sample was brought to room temperature and sodium acetate reagent (58.4 g) was added to a final concentration of 3% (w/v).

(2) Serological Probe: An isopropanol (IPA) fractionation pilot study and antibody-directed end-point Nephelose assay, performed on a 10 mL portion of the sample, showed that the Pn 23F Ps would precipitate between 35–45% IPA.

(3) First IPA Addition: The hydrolyzed sample [volume= 1165 mL, from step 1 above] was brought to 41.0% IPA by the addition of 810 mL IPA (added dropwise with stirring at room temperature). The sample was allowed to stir for 15–30 minutes and then centrifuged at 11,000×g for 30 minutes (Beckman JA-10 rotor; 8,000 rpm; 20° C.). The waste pellet was triturated with absolute EtOH in a 250-mL Omnimix jar, then collected on a 60-mL sinter glass funnel. The precipitate was washed directly on the funnel with absolute EtOH, then acetone, and dried in over $CaCl_2$ at room temperature in preparation for analysis.

(4) Second IPA Addition and Product Recovery: The 41.0% IPA supernatant fluid [volume=1925 mL, from step 3 above] was brought to 43.5% IPA by adding 85.0 mL IPA dropwise while stirring at room temperature. The sample was aged and centrifuged as in step 3 above. The pellet was triturated, collected, washed and dried as in step 3 above. The Pn 23F Ps product weighed 1,795 mg.

(5) Dialysis and Lyophilization: A portion (1779 mg) of the Pn-Ps sample, from Step 4 above, was solubilized in 712 mL of distilled $H_2O$ at room temperature for 3–4 hours. The solution (2.5 mg/mL) was transferred to dialysis tubing (12,000 MW cutoff; 45 mm) and dialyzed vs. distilled $H_2O$ at 4° C. for 27 hours with 2 additional changes of distilled $H_2O$. Then the sample was transferred to lyophilization flasks, shell frozen in a dry ice:methanol bath and lyophilized on a Virtis (Freezemobile) lyophilizer for 2–3 days. The recovery of the final Ps product was 1703 mg. The final product had a $K_d$=0.60.

EXAMPLE 9

Conjugation of Outer Membrane Protein Complex with Pn 23F-Ps Intermediate:

a. Preparation of Dowex 50×2 (200–400 mesh) tetrabutylammonium form resin [Dowex 50 ($Bu_4N^+$)] Dowex 50×2 (200–400 mesh) H+ form, (72 g) was slurried in $H_2O$ (The water used throughout these processes was pyrogen-free, sterile, distilled water), charged to a column and washed sequentially with 1] 800 mL of $H_2O$; 2] 400 mL of 6N HCl; 3] 300 mL of $H_2O$ until effluent is neutral to pH paper; 4] 250 g of a 10% aqueous tetrabutylammonium hydroxide solution until effluent is strongly alkaline to pH paper; 5] 750 mL of $H_2O$.

b. Preparation of Pn23F-Ps tetrabutylammonium form [Pn23F ($Bu_4N+$)]:

A 34-mL column of Dowex 50×2 ($Bu_4N^+$) was washed with 70 mL of $H_2O$. A 450 mg portion of sized Pn 23F Ps was covered with 50 mL of $H_2O$ and stirred for 0.5 hr. This solution was applied to the column and allowed to percolate through by gravity (ca. 2 hr). At this point vacuum was applied to bottom of the column and elution (under vacuum) continued for an additional hour. The column was washed with 25 mL of $H_2O$, and the combined effluents were lyophilized affording 0.5 g of the Pn 23F ($Bu_4N^+$) salt. This was stored in a vacuum desiccator over $P_2O_5$ for ca. 17 hr.

c. Preparation of the 1,4-butanediamine derivative of Pn23F-Ps (Pn23F-$BuA_2$)):

The 0.5 g of Pn 23F ($Bu_4N^+$), from step b above, was covered with 25 mL of dimethylsulfoxide (DMSO) and stirred for 15 min. to dissolve. To this was added 22 mg of carbonyl diimidazole (CDI) and the resultant solution stirred at room temperature (r.t.) for 0.5 hr.

A solution containing 507 mg of 1,4-butanediamine dihydrochloride ($BuA_2$·2HCL) in 32 mL of $H_2O$ was prepared and its pH adjusted to 10.23 with 2.5N NaOH. This solution was filtered through a Millex 0.2 μm GV filter and cooled in an ice bath.

The aged DMSO solution was added to the cold $BuA_2$ solution and stirred an additional 1 hr. in the ice bath. It was then aged at r.t. for 1 hr, after which the solution was charged to 2×12" of Spectrapor dialysis tubing, clipped off 1 cm from the top of the liquid and dialyzed vs: 1) 15 L of pH 7.0, 0.1M sodium phosphate buffer for 16 hr; 2) 15 L of pH 7.0, 0.01M sodium phosphate buffer for 10.5 hr; 3) 15 L of pH 7.0, 0.01M sodium phosphate buffer for 12.5 hr; 4) 15 L of $H_2O$ for 10.5 hr. It was then lyophilized to yeld 220 mg of the 1,4-butanediamine derivative of Pn 23F Ps (Pn23F-$BuA_2$)

An NMR spectrum of ca. 6.9 mg showed a "loading" of approximately 23.5 butanediamine residues per 100 repeating units of polysaccharide defined by comparing the integrals of the butanediamine methylenes and the rhamnose methyl (of Pn 23F) resonances.

d. Preparation of the bromoacetylated butanediamine derivative of Pn 23F Ps (Pn23F-$BuA_2$-BrAc):

Pn23F-$BuA_2$ (214 mg) was covered with 23 mL of a 0.1M, pH 9.0 borate-phosphate buffer and stirred for 30 min. to effect solution. Then 230 mg p-nitrophenyl bromoacetate in 6 mL of acetonitrile was added. The resulting mixture was stirred for 23 hr. at 4° C. It was then dialyzed in Spectrapor 2 tubing vs: 1) 15 L $H_2O$ for 8 hr, 2) 15 L of $H_2O$ for 12 hr and 3) 15 L of $H_2O$ for 6 hr. From the dialyzed contents of the bag were removed 1.5 mL for assays and then 490 mg of dried pH 8.0 phosphate buffer salt (prepared by lyophilizing a 0.1M sodium phosphate pH 8.0 solution) was added. Dissolution requires about 15 min. after which time it is filtered through a 0.2 μm Corning filter affording an aqueous pH 8.0 solution of Pn23F-$BuA_2$-BrAc.

e. Conjugation of OMPC to Pn 23F-$BuA_2$-BrAc-Ps:

Sixty mL OMPC (3.1 mg/mL) was charged to six 10-mL centrifuge tubes and centrifuged in a Beckman 80 Ti rotor at 43,000 rpm (43K), at 4° C. for 2 hr. A thiolation mixture was prepared by dissolving 260 mg of EDTA (ethylenediamine tetraacetic acid disodium salt) and 52 mg of dithiothreitol (DTT) in 30 mL of $Na_2B_4O_7$ thiolactone was added and the solution filtered through a 0.2-μm Corning filter (cup type).

The pellets from the above centrifugation were each dislodged with 3 mL of the filtered thiolation mixture (20 mL total) and transferred to a Dounce homogenizer and resuspended. The tubes were rinsed by serial transfer of an additional 6 mL of the thiolation solution. The rinsing process was repeated with an additional 4 mL of thiolation solution. The combined rinses were homogenized in the Dounce and the total resuspended material (28 mL) was transferred to a 100-mL round-bottom flask.

After sealing with a septum and replacing the air with $N_2$ using a Firestone valve, the reaction mixture was aged for 19 hr. The 28 mL reaction mixture was then divided among three centrifuge tubes, each of which was topped with 1M potassium phosphate (aqueous) and then centrifuged for 2 hr at 43K rpm and 4° C. in a Beckman 80 Ti rotor. The supernatant fluids were removed and the pellets resuspended in 0.1M sodium phosphate, pH 8.0 buffer (a total of 30 mL was the final resuspension volume).

A second ultra-centrifugation (2 hr, 4° C., 43K rpm) was then effected. After removing the supernatant fluid, the pellets were resuspended by the Dounce method in the filtered Pn23F-BuA$_2$-BrAc solution prepared in section 7.I.C.3d. An Ellman assay at this point indicated a total of about 28 μmoles of thiol in the resulting solution.

It should be noted that the filtration of the Pn23F-BuA$_2$-BrAc solution occurs just prior to the resuspension of the thiolated protein. The resultant reaction (i.e., Pn23F-BuA$_2$-BrAc with thiolated OMPC) was aged under N$_2$ (with degassing) in a N$_2$ box at r.t. for 117 hr.

The reaction was then capped (i.e., the reactive moieties on the Pn 23F Ps and OMPC are deactivated) as follows: A solution containing 75 mg N-ethylmaleimide (NEM) in 5 mL of pH 8.0, 0.1M sodium phosphate buffer was filtered through a 0.22-μm filter, was added to the reaction and aged for 18 hr.

The total volume of capped conjugation mixture was 38.5 mL and 1.5 mL of pH 8.0, 0.1M sodium phosphate buffer was added to bring the total volume to 40 mL. Thirty-five mL of this solution was charged equally to four 10 mL centrifuge tubes and each of which was topped with 0.1M pH 8 sodium phosphate buffer. These were centrifuged at 43K rpm, 2 hr., 4° C. The supernatant fluids were removed and each of the pellets was dislodged with 8 mL of TED buffer (1M Tris, pH 8.5, 0.01M EDTA, 0.5% Na deoxycholate) and transferred to a Dounce homogenizer. The centrifuge tubes were serially rinsed with an additional 8 mL of TED buffer and the pellets resuspended (40 mL total) and aged at room temperature for 20 hr. The aged material was centrifuged (as described above) in four 10 mL tubes at 43K, 2 hr., 4° C. Each of the pellets was dislodged with 8 mL of TED buffer, the tubes serially rinsed with 8 mL of TED buffer, resuspended and centrifuged as described above. These pellets were then resuspended in a total of 40 mL of 0.1M pH 7 sodium phosphate buffer and recentrifuged as described above. The pellets were resuspended in a total of 44 mL of water and aged at 4° C. for 17 hrs. A small amount of insolubles were removed by a low speed centrifugation (1000 rpm, 3.5 min.) affording the product in the supernatant fluid.

The resultant supernatant fluid is the drug substance, bulk conjugate vaccine. The conjugate had the following analytical characteristics:

| Test | Results |
|---|---|
| a. Ps Content | 284 mcg/mL |
| b. Protein | 2025 mcg/mL |
| Ps/Protein ratio (Calc.) | 0.14 |
| c. Free Ps | <5 area % |
| d. Amino Acid Analysis | |
| SCMHC/lysine | 6.7% |
| SCMC/lysine | 1.6% |

EXAMPLE 10

Preparation of Pn-Ps by Gaulin Homogenization:

Crude pneumococcal powder was solubilized at a concentration of 1.5 mg/mL in water by mixing overnight at 4° C. A more concentrated solution of Pn-Ps was also prepared at 10 mg/mL. Addition of 50 mM CaCl$_2$ was successful in reducing the viscosity of the 10 mg/mL solution to the viscosity of the 1.5 mg/mL solution. The solubilized Pn-Ps was then passed through a Gaulin homogenizer set at one of four pressure settings: 2000, 5000, 10000, or 15000 PSI. The sheared Pn-Ps was then collected by addition of 60% isopropanol made 50 mM in CaCl$_2$ from a 2M stock. The pellet was washed with 100% ethanol in an omni-mixer, and filtered to recover the precipitated Pn-Ps. The Pn-Ps is washed on the filter with acetone and then dried over CaSO$_4$ (drierits) and stored at −70° C. until analyzed. Aliquots of the sheared Pn-Ps are resuspended at about 1 mg/mL and analyzed for molecular size and polydispersity by HPSEC-universal calibration and for antigenicity index by rate nephelometry:

| Pn-Ps sub-type | MW at which antigenicity begins to decline | Poly-dispersity |
|---|---|---|
| 6B | 500,000 | 1.19 |
| 14 | 300,000 | 1.15 |
| 19F | 250,000 | 1.09 |
| 23F | 250,000 | 1.15. |

EXAMPLE 11

Mouse T-Cell Stimulation:

This test was performed to establish the T-cell dependency/immunogenicity in mice of Pn-Ps Conjugate Vaccines. This model was adopted because children less than two years of age normally respond well to T-dependent antigens. Athymic mice have an abnormal thymic epithlium and therefore their response to T-dependent antigens is significantly less than their normal congenic littermates.

A single dilution of vaccine to give a dosage of 0.5 μg polysaccharide was injected intraperitoneally into adult athymic mice (nu/nu) and their congenic control littermates (nu/+) on day 0, 7 and 28. The mice were bled one week later and their individual sera were tested for antibody response by radioimmunoassay (RIA).

In the RIA, each mouse serum was combined with $C^{14}$ labeled Pn-Ps. Any antigen-antibody complex formed was then precipitated by addition of saturated ammonium sulfate. Each processed sample was counted in a beta counter for one minute. The Pn6B-Ps-OMPC, Pn14-Ps-OMPC, Pn19F-Ps-OMPC, Pn23F-Ps-OMPC, Pn18C-Ps, and Pn4-Ps conjugates of this invention were tested in this manner and found to elicit good T-cell stimulation in the Nu/+ mice.

EXAMPLE 12

Immunogenicity of Pn-Ps Conjugates in Infant Rhesus Monkeys:

This test is performed to establish the immunogenicity in infant monkeys of either bulk conjugate or filled containers of Pn-Ps-OMPC or Pn-Ps-MIEP conjugate vaccine. The infant monkey model has been shown to be an excellent clinical predictor for the PEDVAXHIB™ conjugate vaccine [Vella et al., *Pediatrics*, April 5 Suppl., pp 668–675 (1990)] and was therefore selected as a model for Pn-Ps conjugate vaccine evaluation.

A dose of vaccine is injected intramuscularly (0.25 mL into each of two sites) into 2- to 3-month-old infant monkeys on day 0 and 28. Monkeys are bled on day 0, 28, and day 42 and the individual sera are tested for antibody response by radioimmunoassay (RIA).

In the RIA, each monkey serum is combined with $C^{14}$ labeled Pn-Ps. Any antigen-antibody complex formed is then precipitated by the addition of saturated ammonium sulfate. Each processed sample is counted in a beta counter for one minute. The immunogenic response to the vaccine is satisfactory if at least 50% of the test animals have at least a 1 μg antibody response after receiving two doses of vaccine.

Pn6B-Ps-OMPC, Pn23F-Ps-OMPC, Pn19F-Ps-OMPC, Pn18C-Ps-OMPC, Pn4-Ps-OMPC and Pn14-Ps-OMPC, have been shown to elicit strong anti-type-specific antibody responses. In addition, a tetravalent composition comprising Pn6B-Ps-OMPC, Pn23F-Ps-OMPC, Pn19F-Ps-OMPC, and Pn14-Ps-OMPC, exhibited good anti-Pn-Ps antibody responses to all four serotypes.

EXAMPLE 13

Protective Efficacy of Pneumococcal Conjugates In Chinchillas:

Each Chinchilla was injected subcutaneously or intramuscularly with 0, 0.25, 1.0, or 4.0 μg of Pn6B-Ps-OMPC adsorbed to $Al(OH)_3$. The Chinchillas were bled at 0, 2,4,6, and 8 weeks. The animals were challenged with *Streptococcus pneumoniae* 6B eight weeks after injection and monitored every 1–3 days by otoscopy and tympanometry. Middle ear effusions were aspirated for culture and the animals were sacrificed two weeks post challenge. The sacrificed animals were analyzed for middle ear histopathology. There was 60% mortality in animals receiving no conjugate while even the lowest dose resulted in 0% mortality. There was no protection against purulent otitis media in animals that did not receive conjugate while those receiving conjugate were protected at levels between 60 and 100% across all dosage ranges.

EXAMPLE 14

Anti-Pneumococcal Immune Responses in 2–5 Year Old Children:

2–5 year old children receiving two doses each of 0.5 or 5 μg Pn6B-Ps were tested for production of anti-Pn6B-Ps antibodies by RIA and ELISA. Significant elevations in anti-Pn6B-Ps antibodies were observed.

EXAMPLE 15

Rate Nephelometry of Pneumococcal Polysaccharides:

The purpose of this assay is to determine the polysaccharide content and antigenicity index of free Pn-Ps and conjugate preparations using rate nephelometry.

The range of the standard curve for the rate nephelometry differs for the various Pn-Ps as the response per unit Pn-Ps mass, and the linear portion of the response versus Pn-Ps antigen concentration profile differs for each PnPs. The procedural example given here is specific for Pn6B conjugate and does not necessarily apply for conjugates of other Pn-Ps types. Additionally, alum-adsorbed samples and their respective standards are diluted in 3% sodium citrate rather than 0.9% NaCl, as described below. Aqueous conjugate samples and standards (i.e. those not on alum) are diluted in 0.9% NaCl, and again are diluted to nominal concentrations that are expected to be within the limits of the standard curve.

A) Reagents

Saline solution: 0.9% aqueous NaCl Anti-Pn-Ps sera: Antisera (Health Research, Inc., Albany, N.Y.) is diluted 30-fold with saline solution.

Standards: Prepare 1.0, 1.5, 2.0, 2.5, 3.0 and 4.0 mcg/mL Pn-Ps conjugate standards from a 387 μg/mL stock solution, the concentration of which was determined by the phenol sulfuric acid assay for polysaccharide.

Test Samples: Prepare in sodium citrate stock to have a final concentration of 3% sodium citrate and serial dilutions of the test samples to theoretical concentrations of 1.0, 2.0 and 3.0 mcg of Pn-Ps/ml.

b) Procedure

Assay all samples and standards using the Beckman ICS rate nephelometer using duplicate measurements. Determine the concentration in the samples from the standard curve. Multiply the sample concentration by the dilution factor and average the values for each test sample.

As noted previously, samples found by this method to have antigenicity indexes below 70% are rejected for conjugation to ensure that the Pn-Ps being used has the desired immulogical characteristics.

EXAMPLE 16

Cloning of Genomic DNA Encoding MIEP:

About 0.1 g of the phenol inactivated *N. meningitidis* cells (see Example 1) was placed in a fresh tube. The phenol inactivated cells were resuspended in 567 μL of TE buffer [10 mM TRIS-HCl, 1 mM EDTA, pH 8.0]. To the resuspended cells was added 30 μL of 10% SDS, and 3 μL of 20 mg/mL proteinase K (Sigma). The cells were mixed and incubated at 37° C. for about 1 hour, after which 100 μL of 5M NaCl was added and mixed thoroughly. 80 μL of 1% cetyltrimethylammonium bromide (CTAB) in 0.7M NaCl was then added, mixed thoroughly, and incubated at 65° C. for 10 minutes. An equal volume (about 0.7 to 0.8 mL) of chloroform/isoamyl alcohol (at a ratio of 24:1, respectively) was added, mixed thoroughly and centrifuged at about 10,000×g for about 5 minutes. The aqueous (upper) phase was transferred to a new tube and the organic phase was discarded. An equal volume of phenol/chloroform/isoamyl alcohol (at a ratio of 25:24:1, respectively) was added to the aqueous phase, mixed thoroughly, and centrifuged at 10,000×g for about 5 minutes. The aqueous phase (upper) was transferred to a new tube and 0.6 volumes (about 420 μL) of isopropyl alcohol was added, mixed thoroughly, and the precipitated DNA was centrifuged at 10,000×g for 10 minutes. The supernatant fluid was discarded, and the pellet was washed with 70% ethanol. The DNA pellet was dried and resuspended in 100 μL of TE buffer, and represents *N. meningitidis* genomic DNA.

Two DNA oligonucleotides were synthesized which correspond to the 5' end of the MIEP gene and to the 3' end of the MIEP gene [Murakami, E. C. et al., (1989), *Infection and Immunity*, 57, pp.2318–23]. The sequence of the DNA oligonucleotide specific for the 5' end of the MIEP gene was: 5'-ACTAGTTGCAATGAAAAAATCCCTG-3' (Seq. Id: 1:); and for the 3' end of the MIEP gene was: 5'-GAATTCAGATTAGGAATTTGTT-3' (Seq. Id: 2:).

These DNA oligonucleotides were used as primers for polymerase chain reaction (PCR) amplification of the MIEP gene using 10 nanograms of *N. meningitidis* genomic DNA. The PCR amplification step was performed according to the procedures supplied by the manufacturer (Perkin Elmer).

The amplified MIEP DNA was then digested with the restriction endonucleases SpeI and EcoRI. The 1.3 kilobase (kb) DNA fragment, containing the complete coding region of MIEP, was isolated by electrophoresis on a 1.5% agarose gel, and recovered from the gel by electroelution [Current Protocols in Molecular Biology, (1987), Ausubel, R. M., Brent, R., Kingston, R. E., Moore, D. D., Smith, J. A., Seidman, J. G. and Struhl, K., eds., Greene Publishing Assoc.]

The plasmid vector pUG-19 was digested with SpeI and EcoRI. The gel purified SpeI-EcoRI MIEP DNA was ligated into the SpeI-EcoRI pUG-19 vector and was used to transform E. coli strain DH5. Transformants containing the pUG-19 vector with the 1.3 kbp MIEP DNA were identified by restriction endonuclease mapping, and the MIEP DNA was sequenced to ensure its identity.

EXAMPLE 17

Construction of the pC1/1.Gal10p(B)ADH1$_t$ vector:

The Gal 10 promoter was isolated from plasmid YEp52 [Broach, et al., (1983) in *Experimental Manipulation of Gene Expression*, Inouye, M(Ed) Academic Press pp. 83–117] by gel purifying the 0.5 kilobase pair (kbp) fragment obtained after cleavage with Sau 3A and Hind III. The ADH1 terminator was isolated from vector pGAP.tADH2 [Kniskern, et al., (1986), *Gene*, 46, pp. 135–141] by gel purifying the 0.35 kbp fragment obtained by cleavage with Hind III and SpeI. The two fragments were ligated with T4 DNA ligase to the gel purified pUC18ΔHind III vector (the Hind III site was eliminated by digesting pUC18 with Hind III, blunt-ending with the Klenow fragment of E. coli DNA polymerase I, and ligating with T4 DNA ligase) which had been digested with BamHI and SphI to create the parental vector pGal10-tADH1. This has a unique Hind III cloning site at the Gal10p.ADH1$_t$ junction.

The unique Hind III cloning site of pGal10.tADH1 was changed to a unique BamHI cloning site by digesting pGal10.tADH1 with Hind III, gel purifying the cut DNA, and ligating, using T4 DNA ligase, to the following Hind III-BamHI linker:

5'-AGCTCGGATCCG-3'
3'-GCCTAGGCTCGA-5' (Seq. Id:3:).

The resulting plasmid, pGal10(B)tADH1, has deleted the Hind III site and generated a unique BamHI cloning site.

The Gal10p.tADH1 fragment was isolated from pGal10(B)tADH1 by digestion with SmaI and SphI, blunt-ended with T4 DNA polymerase, and gel purified. The yeast shuttle vector pC1/1 [Brake et al., (1984), *Proc. Nat'l. Acad. Sci. USA*, 81, pp.4642–4646] was digested with SphI, blunt-ended with T4 DNA polymerase, and purified. This fragment was ligated to the vector with T4 DNA ligase. The ligation reaction mixture was then used to transform E. coli HB101 cells to ampicillin resistance, and transformants were screened by hybridization to a single strand of the 32P-labelled HindIII-BamHI linker. The new vector construction, pC1/1.Gal10p(B)ADH1$_t$ was confirmed by digestion with HindIII and BamHI.

EXAMPLE 18

Construction of a Yeast MIEP Expression Vector with MIEP+Leader DNA Sequences

A DNA fragment containing the complete coding region of MIEP was generated by digestion of pUC19.MIEP #7 with SpeI and EcoRI, gel purification of the MIEP DNA, and blunt-ended with T4 DNA polymerase.

The yeast internal expression vector pC1/1.Gal10p(B)ADH1$_t$ was digested with Bam HI, dephosphorylated with calf intestinal alkaline phosphatase, and blunt-ended with T4 DNA polymerase. The DNA was gel purified to remove uncut vector.

The 1.1 kbp blunt-ended fragment of MIEP was ligated to the blunt-ended pC1/1.Gal10p(B)ADH1$_t$ vector, and the ligation reaction mixture was used to transform competent E. coli DH5 cells to ampicillin resistance. Transformants were screened by hybridization to a $^{32}$P-labelled DNA oilgoncleotide:

5' . . . AAGCTCGGATCCTAGTTGCAATG . . . 3' (Seq. Id: 4:), which was designed to be homologous with sequences overlapping the MIEP-vector junction. Preparations of DNA were made from hybridization positive transformants and digested with KpnI and SalI to verify that the MIEP fragment was in the correct orientation for expression from the Gal 10 promoter. Further confirmation of the DNA construction was obtained by dideoxy sequencing from the Gal10 promoter into the MIEP coding region.

Expression of MIEP by the transformants was detected by Western blot analysis. Recombinant MIEP produced in the transformants comigrated on polyacrylamide gels with MIEP purified from OMPC vesicles, and was immunologically reactive with antibodies specific for MIEP.

EXAMPLE 19

Construction of yeast MIEP expression vector with a 5'-Modified MIEP DNA Sequence.

A DNA oligonucleotide containing a HindIII site, a conserved yeast 5' nontranslated leader (NTL), a methionine start codon (ATG), the first 89 codons of the mature MIEP (beginning with Asp at position +20) and a KpnI site (at position +89) was generated using the polymerase chain reaction (PCR) technique. The PCR was performed as specified by the manufacturer (Perkin Elmer Cetus) using the plasmid pUC19MIEP42#7 as the template and the following DNA oligomers as primers:

$^5$'CTAAGCTTAACAAAATGGACGTTACCTTGTACGGTACAATT$^3$' (Seq. Id:5:), and
$^5$'ACGGTACCGAAGCCGCCTTTCAAG$^3$' (Seq. Id:6:).

To remove the 5' region of the MIEP clone, plasmid pUC19MIEP42#7 was digested with KpnI and HindIII and the 3.4 kbp vector fragment was agarose gel purified. The 280 bp PCR fragment was digested with KpnI and HindIII, agarose gel purified, and ligated with the 3.4 kbp vector fragment. Transformants of E. coli HB101 (BRL) were screened by DNA oligonucleotide hybridization and the DNA from positive transformants was analyzed by restriction enzyme digestion. To ensure that no mutations were introduced during the PCR step, the 280 bp PCR generated DNA of the positive transformants was sequenced. The resulting plasmid contains a HindIII—EcoRI insert consisting of a yeast NTL, ATG codon, and the entire open reading frame (ORF) of MIEP beginning at the Asp codon (amino acid +20).

The yeast MIEP expression vectors were constructed as follows. The pGAL10/pC1/1 and pGAP/pC1/1 vectors [Vlasuk, G. P., et al., (1989) J. B. C., 264, pp.12,106–12,112] were digested with BamHI, flush-ended with the Klenow fragment of DNA polymerase I, and dephosphorylated with calf intestinal alkaline phosphatase. These linear vector's were ligated with the Klenow treated and gel purified HindIII—EcoRI fragment described above, which contains the yeast NTL, ATG and ORF of MIEP are forming pGal10/pC1/1-MIEP and pGAP/pC1/1-MIEP.

*Saccharomyces cerevisiae* strain U9 (gal10pga14-) were transformed with plasmid pGal10/pC1/1-MIEP. Recombinant clones were isolated and examined for expression of MIEP. Clones were grown at 37° C. with shaking in synthetic medium (leu-) containing 2% glucose (w/v) to an $O.D._{660}$ of about 6.0. Galactose was then added to 2% (w/v) to induce expression of MIEP from the Gal10 promoter. The cells were grown for an additional 45 hours following galactose induction to an $O.D._{600}$ of about 9.0. The cells were then harvested by centrifugation. The cell pellet was washed with distilled water and frozen.

Western Blot For Recombinant MIEP:

To determine whether the yeast was expressing MIEP, Western blot analysis was done. Twelve percent, 1 mm, 10 to 15 well Novex Laemmli gels are used. The yeast cells were broken in $H_2O$ using glass beads (sodium dodecylsulfate (SDS) may be used at 2% during the breaking process). Cell debris was removed by centrifugation for 1 minute at 10,000×g.

The supernatant was mixed with sample running buffer, as described for polyacrylamide gel purification of MIEP. The samples were run at 35 mA, using OMPC as a reference control, until the bromophenol blue dye marker runs off the gel.

Proteins were transferred onto 0.45µ pore size nitrocellulose paper, using a NOVEX transfer apparatus. After transfer the nitrocellulose paper was blocked with 5% bovine serum albumin in phosphate buffered saline for 1 hour, after which 15 mL of a 1:1000 dilution of rabbit anti-MIEP antiserum (generated by immunization with gel purified MIEP using standard procedures) was added. After overnight incubation at room temperature 15 mL of a 1:1000 of alkaline phosphatase conjugated goat anti-rabbit IgG was added. After 2 hours incubation the blot was developed using FAST RED TR SALT (Sigma) and Naphthol-AS-MX phosphate (Sigma).

EXAMPLE 20

Bacterial Expression Of Recombinant MIEP

Plasmid pUC19-MIEP containing the 1.3 kilobase pair MIEP gene insert, was digested with restriction endonucleases SpeI and EcoRI. The 1.1kbp fragment was isolated and purified on an agarose gel using standard techniques known in the art. Plasmid pTACSD, containing the two cistron TAC promoter and a unique ECORI site, was digested with EcoRI. Blunt ends were formed on both the 1.3 kbp MIEP DNA and the pTACSD vector, using T4 DNA polymerase (Boehringer Mannheim) according to the manufacturer's directions. The blunt ended 1.3 kbp MIEP DNA was ligated into the blunt ended vector using T4 DNA ligase (Boehringer Mannheim) according to the manufacturer's directions. The ligated DNA was used to transform *E. coli* strain DH5aIQMAX (BRL) according to the manufacturer's directions. Transformed cells were plated onto agar plates containing 25 µg kanamycin/mL and 50 µg penicillin/mL, and incubated for about 15 hours at 37° C. A DNA oligonucleotide with a sequence homologous with MIEP was labelled with $^{32}P$ and used to screen nitrocellulose filters containing lysed denatured colonies from the plates of transformants using standard DNA hybridization techniques. Colonies which were positive by hybridization were mapped using restriction endonucleases to determine the orientation of the MIEP gene.

Expression of MIEP by the transformants was detected by Western blot analysis. Recombinant MIEP produced in the transformants co-migrated on polyacrylamide gels with MIEP purified from OMPC vesicles, and was immunologically reactive with antibodies specific for MIEP.

EXAMPLE 21

Conjugation of Pn-Ps to *N. meningitidis* MIEP:

Chemical conjugations are conducted according to the method disclosed in U.S. Pat. No. 4,882,317.

10 mg of MIEP in 3 mL of 0.1M borate buffer, pH 11.5, are mixed with 10 mg of ethylenediamine tetraacetic acid disodium salt (EDTA, Sigma chemicals) and 4 mg of dithiothreitol (Sigma Chemicals). The protein solution is flushed thoroughly with $N_2$. 125 mg of N-acetylhomocysteinethiolactone (Aldrich Chemicals) is added to the MIEP solution, and the mixture is incubated at room temperature for 16 hours. It is then twice dialyzed under $N_2$ against 2 L of 0.1M borate buffer, pH 9.5, containing 4 mM EDTA, for 24 hours at room temperature. The thiolated protein is then assayed for thiol content by Ellman's reagent (Sigma Chemicals) and the protein concentration is determined by Bradford reagent (Pierce Chemicals). For conjugation of MIEP to Pn-Ps, a 1.5 fold excess (wt/wt) of bromoacetylated Pn-Ps is added to the MIEP solution and the pH is adjusted to 9–9.5 with 1N NaOH. The mixture is allowed to incubate under $N_2$ for 6 to 8 hours at room temperature. At the end of the reaction time, 25 μL of N-acetylcysteamine (Chemical Dynamics) is added to the mixture, and is allowed to stand for 18 hours under $N_2$ at room temperature. The conjugate solution is acidified to between pH 3 to 4 with 1N HCl, and centrifugation is conducted at 10,000×g for 10 minutes. 1 mL of the supernatant fluid is applied directly onto a column of FPLC Superose 6B (1.6×50 cm, Pharmacia) and the conjugate is eluted with PBS. The void volume peak which contains the polysaccharide-protein conjugate (Pn-Ps-MIEP), is pooled. The conjugate solution is then filtered through a 0.22 μm filter for sterilization.

EXAMPLE 22

Demonstration of Immunogenicity of Pn-Ps-MIEP Conjugates:

Immunizations: Male Balb/c mice (Charles River, Wilmington, Mass.) are immunized IP with Pn-Ps covalently conjugated to MIEP using 2.5 μg Pn-Ps in 0.5 mL of preformed alum. Control mice are immunized with equivalent amounts of Pn-Ps given as Pn-Ps-CRM [Anderson, M. E. et al., (1985), *J. Pediatrics,* 107, pp. 346–351] (2.5 μg Pn-Ps/6.25 μg CRM; ¼ of the human dose), Pn-Ps-DT (2.5 μg Pn-Ps/1.8 μg DT; ⅒ of the human dose such that constant amounts of Pn-Ps are used), and Pn-Ps-OMPC (2.5 μg Pn-Ps/35 μg OMPC; ¼ of the human dose).

Infant Rhesus monkeys, 6–13.5 weeks of age, are immunized with Pn-Ps-MIEP conjugates adsorbed onto alum. Each monkey receives 0.25 mL of conjugate at two different sites of injection, for a total dose of 0.5 mL. The monkeys are immunized on day 0, 28, and 56, and blood samples are taken every two to four weeks.

Antibody responses are measured by the ELISA, which distinguishes the class and subclass of the immunoglobulin response. An RIA which quantitates the total anti-Pn-Ps antibody is also used to evaluate the monkey response.

Pn-Ps-MIEP conjugates are capable of generating an immune response in mice consisting of IgG anti-Pn-Ps antibody and a memory response. This is in contrast to the Pn-Ps-CRM and Pn-Ps-DT which do not elict measurable anti-Pn-Ps antibody. Thus, MIEP functions as an immunologic carrier protein for Pn-Ps and is capable of engendering an anti-Pn-Ps antibody response when covalently conjugated to the Pn-Ps antigen. Purified MIEP is therefore an effective immunologic carrier protein replacing the heterogeneous OMPC in construction of bacterial polysaccharide conjugate vaccines.

EXAMPLE 23

Quantitative Determination of C-Polysaccharide Content in Pn-Ps Preparations:

Systems have been developed for quantitation of C-polysaccharide, based on NMR, enzymatic, or chromatographic methods. In the instant case, the chromatographic separation of choline (a component of C-Ps) from samples of hydrolyzed Pn-Ps, was used and compared with these other methods. The choline was separated on a cation exchange column coupled with suppressed conductivity detection.

Samples of Pn-Ps were completely hydrolyzed by treatment with 36% hydrofluoric acid for 2 hours at 45°–65° C. followed by 2M trifluoroacetic acid for 16 hours at 100° C. Following hydrolysis, 200–300 µg of the sample was injected onto a Dionex BioLC Chromatography system, having an Omnipac PCX-500 analytical and guard column, an Ion Pac CTC-1 cation trap column, a CMMS-2 Micromembrane Suppressor, regenerated with 50 mM tetrabutylammonium hydroxide (10 ml/min), and the conductivity detector set at 1 µSiemen sensitivity. The sample was eluted isocratically using 5% 200 mM HCl, 5% 20% Acetonitrile, 85% MilliQ water, 5% 20 mM diaminopropionic acid. Choline eluted as a sharp peak after approximately 10 minutes.

Purified C-Ps (obtained from Statens Serum Institut) was analyzed for choline content using this method and a value of 5.4% choline by weight was obtained. This value agrees with published reports of choline content of C-PS.

This factor was used to calculate the C-Ps concentration in various samples of Pn-Ps preparations by converting the nanomole quantities of choline obtained by HPLC to mass values. Using the conversion of 5.4% choline by weight, the mass of C-Ps by weight was calculated. Samples having C-Ps concentrations over 3% were rejected as unacceptable for conjugation. The table below shows the correlation of this method with the NMR and enzymatic methods, and shows typical C-Ps contamination levels in preparations of Pn-Ps of varying degrees of purity:

| Sample | NMR | ENZYMATIC | HPLC |
| --- | --- | --- | --- |
| Pn6B-Ps | 20% | N.D. | 18.4% |
| Pn6B-Ps | 1.6% | 0.3–1.0% | 1.2% |
| Pn23F-Ps | N.D. | 2.8% | 3.7% |
| Pn14-Ps | 2.9% | 2.4% | 3.2% |
| Pn19F-Ps | 2.7% | 2.6% | 2.6% |

EXAMPLE 24

Preparation of Partially-Hydrolyzed, Purified Pn18C-Ps:

(1) Sonic Hydrolysis: A 3.0-g portion of Pn 18C Ps powder was solubilized in 1200 mL saline (0.9% NaCl) with stirring at room temperature for about 3–4 hours, then covered and stored at 4° C. overnight. The solution then was sonicated in a plastic beaker in an ice bath with a Branson Sonifier (one-half inch pobe, setting 8) for intervals of 20 minutes (in 5-minute bursts) up to 40 minutes total. The viscosity was checked after each interval. After 40 minutes, another 10 minute sonication was performed to obtain a viscosity endpoint of 1.218 centistokes. The hydrolyzed sample (volume-1188mL) was brought to room temperature and sodium acetate reagent (59.2 g) was added to a final concentration of 3% (w/v).

(2) Serological Probe: An isopropanol (IPA) fractionation probe and antibody-directed end-point Nephelose assay, performed on a 10 mL portion of the sample, showed that the Pn18C-Ps would precipiate between 40–50% IPA.

(3) First IPA addition: the hydrolyzed sample [volume= 1200 mL, from step 1 one above] was brought to 42.7% IPA by the addition of 894 mL IPA (added dropwise with stirring at room temperture). The sample was allowed to stir for 15–30 minutes and then centrifuged at 11,000×g for 30 minutes (Beckman JA-10 rotor; 8,000 rpm; 20° C.). The waste pellet was triturated with absolute EtOH in a 250-mL Omnimix jar, then collected on a 60-mL sinter glass funnel. The precipitate was washed directly on the funnel with absolute EtOH, then acetone, and dried in vacuo over $CaSO_4$ (Drierite) at room temperature in preparation for analysis.

(4) Second IPA Addition and Intermediate Product Recovery: The 42.7% IPA supernatant fluid [volume=2016 mL, from step 3 above] was brought to 45.2% IPA by adding 92.0 mL IPA dropwise while stirring at room temperature. The sample was aged and centrifuged as in step 3 above. The pellet was triturated, collected, washed and dried as in step 3 above. The Pn18C-Ps intermediate product weighed 1,609 mg.

(5) Dialysis and Lyophilization: A portion (1612.5 mg) of sample from Step 4 above, was solubilized in 645 mL of distilled $H_2O$ at room temperature for about 2 hours. The solution (2.5 mg/mL) was transferred to dialysis tubing (12,000 MW cutoff; 45 mm) and dialyzed vs. distilled $H_2O$ at 4° C. for 30 hours with 2 additional change of distilled $H_2O$. Then the sample was transferred to lyophilization flasks, shell frozen in a dry ice: methanol bath and lyophilized on a Virtis (Freezemobile) lyophilizer for 2–3 days. The recovery of the final Ps product was 1487 mg.

EXAMPLE 25

*S. Pneumoniae* 18C-OMPC Conjugate, Pn18C-Ps-OMPC:

A. Preparation of Dowex 50×2 (200–400 mesh) tetrabutylammonium form resin [Dowex 50 ($Bu_4N^+$)] Dowex 50×2

(200–400 mesh) H+ form, (500 g) was slurried in $H_2O$, charged to a column and washed sequentially with 1] 600 mL of $H_2O$; 2] 1000 mL of 6 n HCl; 3] 400 mL of $H_2O$ until effluent was neutral to pH paper; 4]72 g of a 10% aqueous tetrabutylammonium hydroxide solution until effluent was strongly alkaline to pH paper; 5] 1000 mL of $H_2O$ to neutrality.

B. Preparation of *S. Pneumoniae* type 18C polysaccharide tetrabutylammonium form [Pn18C($Bu_4N^+$)]: A 60 mL column of Dowex 50×2 ($Bu_4N^+$) was washed with 250 mL of $H_2O$. Pn18C-polysaccharide (m.w. reduced(650 mg) was covered with 65 mL of $H_2O$ and stirred for 1 hr at which time all seemed to be in solution. This solution was applied to the column and allowed to percolate through by gravity (for 2 hr then under vacuum for 1 hr). The column was washed with 150 mL of $H_2O$ and the combined effluents were lyophilized affording 655 mg of the 18C ($Bu_4N^+$) salt. Twenty five mg was removed for nmr analysis and retained material.

C. Preparation of the 1,4-butane diamine derivative of 18C (18C-$BuA_2$): 18C ($Bu_4N^+$) (630 mg) was covered with 143 mL of DMSO (dimethylsulfoxide) and stirred for 3.25 hr. At this time all the solid was dissolved and 1 mL was removed for Karl Fischer titration for water content. A value of 28.2 micromoles of $H_2O$/mL was found (4 mmoles total). To this solution was added 165.1 mg of carbonyl diimidazole (CDI) and the resultant solution stirred at room temperature (r.t.) for 2.0 hr. A solution containing 1.260 g of 1,4-butane diamine dihydrochloride ($BuA_2 \cdot 2HCl$) in 40 mL of $H_2O$ was prepared and its pH adjusted to 10.20 with 2.5N NaOH. This solution was cooled in an ice bath. The aged DMSO solution was slowly added to the cold $BuA_2$ solution and stirred an additional 10 min in the ice bath. It was then stirred at r.t. for 50 min, after which the solution was charged to SPECTRAPOR 2 dialysis tubing, clipped off ½" from the top of the liquid and dialyzed as follows vs: 1] 15 L of pH 7.0 0.1M NaPO4 buffer for 13.0 hr; 2] 15 L of pH 7.0 0.01M NaPO4 buffer for 11 hr; 3] 15 L of pH 7.0 0.01M NaPO4 buffer for 10.8 hr; 4] 15 L of H2O for 9.5 hr. The volume at this point was 190 mL. A 7.5 mL aliquot was removed and lyophilized separately for nmr assay. The remaining 182.5 mL was lyophilized to 416 mg of the 1,4-butane diamine derivative of 18C (Pn18C-BuA2). An NMR spectrum of about 5 mg showed a "loading" of 10 butane diamine residues per 100 repeating monomeric units of polysaccharide defined by comparing the integrals of the butanediamine internal methylenes and the rhammose methyls (of 18C) resonances.

D. Preparation of the bromoacetylated butane diamine derivative of 18C (Pn18C-$BuA_2$-BrAc): 18C-BuA2 (416 mg) was covered with 36 mL of a 0.1M pH 9.04 buffer (Kolthoff borate-phosphate) and stirred to effect solution. Then 256 mg p-nitrophenyl bromacetate in 4.48 mL of acetonitrile was added. The resulting mixture was stirred for 20 hrs at 4° C. It was then dialyzed in SPECTRAPOR 2 tubing as follows: 1] vs 15 L $H_2O$ for 6 hr; 2] vs 15 L of $H_2O$ for 6 hr; 3] vs 15 L of H2O for 6 hr. At this point there was a volume of 60 mL from which was removed 1.7 mL for assays (NMR, Ouchterlony and Viscotek) and then 2.42 g of dried pH 8 phosphate buffer salt (prepared by lyophylizing a 0.1M pH 8 NaPO4 solution) was added. After dissolution it was filtered through a 0.2 micron CORNING filter affording an aqueous pH 8 solution of 18C-BuA2-BrAc. The filtration was slow and required 4 cup filters.

E. Conjugation of OMPC (*N. meningitidis*) to Pn18C-$BuA_2$-BrAc: Outer Membrane Protein Complex (*N. meningitidis*, OMPC 3.2 mg/mL, 80 mL was charged to four 25 mL centrifuge tubes and centrifuged in a 60 Ti rotor at 43,000 rpm (43K), at 4° C. for 2 hr. A thiolation mixture was prepared by dissolving 680 mg of EDTA (ethylene diamine tetracetic acid disodium salt) and 120 mg of dithiothreitol (DTT) in 40 mL of a pH 11.09 $Na_2B_4O_7$ buffer. 320 mg of N-acetylhomocysteine thiolactone was added and then the solution filtered through a 0.2µ Corning filter (cup type). The pellets from the above centrifugation were dislodged with 5 mL of the filtered thiolation mixture (20 mL total) and transferred to a DOUNCE homogenizer and resuspended. The tubes were rinsed by serial transfer of an additional ²⁄₁₀ mL of the thiolation solution. The combination solutions were homogenized in the DOUNCE and the total resuspended material (40 mL) was transferred to a 100 mL round bottom flask. The glassware was rinsed with an additional 20 mL of the thiolation solution and added to the reaction flask. After sealing the flask with a septum and replacing the air with $N_2$ using a FIRESTONE valve, the reaction mixture was aged for 18.5 hr. The 60 mL was then divided among four centrifuge tubes, each of which was topped with 1M $KH_2PO_4$ (aqueous) and then centrifuged for 2 hr at 43K and 4° C. The supernatants were removed and the pellets resuspended in 0.1M NaPO4 pH 8 buffer (a total of 40 mL was the final resuspension volume). This solution was transferred equally, to two 25 mL centrifuge tubes (polycarbonate) and the glassware (DOUNCE etc) was rinsed with about 10 mL of pH 8 phosphate buffer and used to top off the centrifuge tubes. A second ultra-centrifugation (2 hr, 4° C., 43K) was then effected. The pellets were resuspended in 30 mL of pH 8, 0.1M PO4 buffer. An Ellman assay indicated a total of 24 micromoles of SH or about 100 nanomoles/mg of OMPC. The thiolated protein was transferred to a 100 mL round bottom flask and the filtered 18C-BuA2-BrAc solution was added to it. The resultant reaction (i.e. 18C-BuA2-BrAc with thiolated OMPC) was aged under N2 (with degassing) in the N2 box at room temperature for 89 hr.

The reaction was then capped as follows: A solution containing 75 mg N-ethylmaleimide (NEM) in 5 mL of pH 8, 0.1M NaPO4 buffer was filtered through a 0.22 micron filter and 2 mL added to the above reaction mixture and aged for 4 hr.

Then 0.5 mL of N-acetylcysteamine in 2.5 mL of 0.1M pH 8 PO4 buffer was filtered through a 0.22 micron filter and 1.0 mL of this solution was added to the reaction and aged for 22.5 hr.

The capped product was then equally charged to four 25 mL centrifuge tubes, and topped with a total of 8 mL of pH 8 0.1M PO4 buffer and centrifuged at 43K, 2 hr, 4° C. After removing the supernatants, the pellets were resuspended in a DOUNCE homogenizer in a total of 40 mL of TED buffer, the glassware rinsed with an additional 10 mL of TED buffer and the solution transferred to two 25 mL tubes. These tubes were stored at room temperature for 15.25 hr and then centrifuged for 2 hr at 43K rpm and at 24° C. The resultant pellets were resuspended in a DOUNCE homogenizer in a total of 30 mL of TED buffer, transferred to two 25 mL centrifuge tubes, the glassware rinsed with an additional 20 mL of TED buffer and recentrifuged at 43K, 4° C. for 2 hr. The pellets were resuspended in 50 mL of pH 7 phosphate buffer and subjected to a third centrifugation at 43K for 2 hr at 4° C. The pellets were resuspended in 82 mL of water and transferred in 20.5 ml portions to two 50 mL plastic sterile (FALCON) centrifuge tubes. After ageing at 4° C. for 18 hr, the conjugate preparation was centrifuged at 1000 RPM for 3.5 minutes, in a TH rotor in a TJ-6 centrifuge. The final product conjugate suspension was assayed for protein (Lowry), 18C polysaccharide (phenol/sulfuric acid), unconjugated polysaccharide (size exclusion chromatography—rate Nephelometry) and amino acids (SPINCO):

Polysaccharide=339 microgram/mL;

Protein=2.57 mg/mL;

Free Polysaccharide: <5% (limit of experimental error);

S-carboxymethylhomocysteine/lysine=0.025;

S-carboxymethylcysteamine/lysine=0.005.

EXAMPLE 26

Preparation of the Pn4-Ps Intermediate:

(1) Sonic Hydrolysis: A 1.0-g portion of Pn4-Ps powder was solubilized in 400 mL saline (0.9% NaCl) with stirring at room temperature for about 4 hours. The solution was then sonicated in a plastic beaker in an ice bath with a Branson Sonifier (one-half inch probe, setting 8) for intervals of 10 minutes, up to 20 min. total. The viscosity was checked after each interval. After 20 min., a viscosity endpoint of 1.267 centistokes was obtained. The hydrolyzed sample was brought to room temperature and sodium acetate reagent (18.7 g) was added to a final concentration of 3% (w/v).

(2) Serological Probe: An isopropanol (IPA) fractionation pilot study and antibody-directed end-point Nephelose assay, performed on a 10 mL portion of the sample, showed that the Pn 4 Ps would precipitate between 45–55% IPA.

(3) First IPA Addition: The hydrolyzed sample [volume= 385 mL, from step 1 above] was brought to 49.7% IPA by the addition of 379 mL IPA (added dropwise with stirring at room temperature). The sample was allowed to stir for 15–30 minutes and then centrifuged at 11,000×g for 30 minutes (Beckman JA-10 rotor; 8,000 rpm; 20° C.). The waste pellet was triturated with absolute EtOH in a 250-mL Omnimix jar, then collected on a 60-mL sinter glass funnel. The precipitate was washed directly on the funnel with absolute EtOH, then acetone, and dried in vacuo over $CaCl_2$ at room temperature in preparation for analysis.

(4) Second IPA Addition and Product Recovery: The 49.7% IPA supernatant fluid [volume=727 mL, from step 3 above] was brought to 52.2% IPA by adding 38 mL IPA dropwise while stirring at room temperature. The sample was aged and centrifuged as in step 3 above. The pellet was triturated, collected, washed and dried as in step 3 above. The Pn 4 Ps product weighed 516 mg.

(5) Dialysis and Lyophilization: A portion (500 mg) of the Pn-Ps sample from Step 4 above was solubilized in 200 mL of distilled $H_2O$ at room temperature for 2–3 hours. The solution (2.5 mg/mL) was transferred to dialysis tubing (12,000 MW cutoff; 45 mm) and dialyzed vs. distilled $H_2O$ at 4° C. for 27 hours with 2 additional changes of distilled $H_2O$. Then the sample was transferred to lyophilization flasks, shell frozen in a dry ice:methanol bath and lyophilized on a Virtis (Freezemobile) lyophilizer for 2–3 days. The recovery of the final Ps product was 491 mg. The final product had a $K_d$=0.69.

From this disclosure it should be obvious to those skilled in the art that other corboxyl containing Pn-Ps subtypes, such as Pn1-Ps or Pn5-Ps, could be prepared according to the method disclosed here, and conjugated as for Pn4-Ps or Pn9V-Ps which are also acidic polysaccharides.

EXAMPLE 27

S. Pneumoniae Type 4-OMPC Conjugate, Pn4-Ps-OMPC:

A. Preparation of Dowex 50×2 (200–400 mesh) tetrabutylammonium form resin [Dowex 50 ($Bu_4N^+$)] Dowex 50×2 (200–400 mesh) H+ form, (500 g) was slurried in $H_2O$ (CM-66), charged to a column and washed sequentially with 1] 600 mL of $H_2O$; 2] 1000 mL of 6n HCl; 3] 400 mL of $H_2O$ until effluent was neutral to pH paper; 4] 72g of a 10% aqueous tetrabutylammonium hydroxide solution until effluent was strongly alkaline to pH paper; 5] 1000 mL of $H_2O$ to neutrality.

B. Preparation of S. Pneumoniae type 4 polysaccharide tetrabutylammonium form [Pn4($Bu_4N^+$)]: A 65 mL column of Dowex 50×2 ($Bu_4N^+$) was washed with 520 mL of $H_2O$. Pn 4-polysaccharide (m.w. reduced (400 mg) was covered with 35 mL of $H_2O$ and stirred for 20 min at which time all seemed to be in solution (stirring was continued overnight). This solution was applied to the column and allowed to percolate through by gravity and the column was washed with 150 mL of $H_2O$ and the combined effluents were lyophilized affording 504 mg of the Pn 4 ($Bu_4N^+$) salt.

C. Preparation of the 1,4-butane diamine derivative of Pn 4 (Pn 4-$BuA_2$) Pn 4 ($Bu_4N^+$) (97 mg) was covered with 16 mL of DMSO (dimethylsulfoxide) and stirred into the solution at 52° C. over a period of 15 min. At this time all the solid was dissolved and the solution was cooled to room temperature.

To this solution was added 2 mg of carbonyl diimidazole (CDI) dissolved in 160 microliters of DMSO and the resultant solution stirred at room temperature (r.t.) for 1.0 hr. A solution containing 0.500 g of 1,4-butane diamine dihydrochloride ($BuA_2$·2HCl) in 5 mL of $H_2O$ was prepared and its pH adjusted to 10.20 with 5.0N NaOH. This solution was cooled in an ice bath. The aged DMSO solution was slowly added to the cold $BuA_2$ solution and stirred an additional 5 min in the ice bath. It was then stirred at r.t. for 1 hr, after which the solution was charged to SPECTRAPOR 2 dialysis tubing, clipped off ½" from the top of the liquid and dialyzed as follows vs: 1] 4 L of pH 7.0 0.1M $NaPO_4$ buffer for 15.0 hr; 2] 4 L of pH 7.0 0.01M $NaPO_4$ buffer for 9 hr; 3] 4 L of pH 7.0 0.01M $NaPO_4$ buffer for 21 hr; 4] 4 L of $H_2O$ for 20 hr. The solution was lyophilized to 70 mg of the 1,4-butane diamine derivative of Pn 4 (Pn 4-$BuA_2$). An NMR spectrum of about 5 mg showed a "loading" of 22 butane diamine residues per 100 repeating monomeric units of polysaccharide defined by comparing the integrals of the butanediamine internal methylenes and the N-acetyl methyls (of Pn 4) resonances.

D. Preparation of the bromoacetylated butane diamine derivative of Pn 4(Pn 4-$BuA_2$-BrAc): Pn 4-$BuA_2$ (54 mg) was covered with 5.5 mL of a 0.1M pH 9.04 buffer (Kolthoff borate-phosphate) and stirred to effect solution. Then 55 mg p-nitrophenyl bromacetate in 1.0 mL of acetonitrile was added. The resulting mixture was stirred for 17 hrs at 4° C. It was then dialyzed in SPECTRAPOR 2 tubing as follows: 1] vs 16 L $H_2O$ for 24 hr; 2] vs 16 L of $H_2O$ for 8 hr; 3] vs 16 L of $H_2O$ for 23 hr. At this point there was a volume of 12.5 mL from which was removed 1.0 mL for assays (NMR, Ouchterlony and Viscotek) and then 275 mg of dried pH 8 phosphate buffer salt (prepared by lyophylizing a 0.1M pH 8 $NaPO_4$ solution) was added. After dissolution it was filtered through a 0.2 micron CORNING filter affording an aqueous pH 8 solution of Pn 4-BuA2-BrAc.

E. Conjugation of OMPC (N. meningitidis) to Pn 4-$BuA_2$-BrAc: Outer Membrane Protein Complex (N. meningitidis, OMPC, 4.34 mg/mL) (5 mL) was centrifuged in a 80 Ti rotor at 43,000 rpm (43K), at 4° C. for 2 hr. A thiolation mixture was prepared by dissolving 85 mg of EDTA (ethylene diamine tetracetic acid disodium salt) and 15 mg of dithiothreitol (DTT) in 10 mL of a pH 11.09 $Na_2B_4O_7$ buffer. 50 mg of N-acetylhomocysteine thiolactone was added and then the solution filtered through a 0.2 m micron filter. The pellets from the above centrifugation were dislodged with 5 mL of the filtered thiolation mixture and transferred to a DOUNCE homogenizer and resuspended. The resuspended solution was transferred to a centrifuge tube, capped with a septum and the air replaced with $N_2$ using a FIRESTONE valve. The reaction mixture was aged for 19 hr and then transferred to a centrifuge tube which was topped with 1M $KH_2PO_4$ (aqueous) and then centrifuged for 2 hr at 43K 4° C. The supernatants were removed and the pellets resuspended in 10 mL of 0.1M $NaPO_4$ pH 8 buffer. This solution was transferred to a centrifuge tube and a second ultracentrifugation (2 hr, 4° C., 43K) was then effected. The pellets were resuspended in 11.5 mL of Pn 4-$BuA_2$-BrAc solution prepared in section D. An Ellman assay indicated a total of 3.44 micromoles of SH or about 158 nanomoles SH/mg of OMPC. The resultant reaction (i.e. Pn 4-$BuA2$-BrAc with thiolated OMPC) was aged under N2 (with degassing) in the N2 box at room temperature for 66 hr.

The reaction was then capped as follows: A solution containing 5 mg N-ethylmaleimide (NEM) in 1 mL of pH 8, 0.1M $NaPO_4$ buffer was filtered through a 0.22 micron filter and added to the above reaction mixture and the solution aged for hr. Then 0.1 mL of N-acetylcysteamine in 0.4 mL of 0.1M pH 8 $PO_4$ buffer was filtered through a 0.22 micron filter and this solution was added to the reaction and aged for 14.5 hr.

The reaction mixture was then centrifuged at 43K,4° C. for 2 hr and the pellet resuspended in 8 mL of 1X TED buffer. This solution was aged at room temperature overnight and then centrifuged at 43K,4° C. for 2 hr. The pellet was resuspended in 2 mL of TED buffer and immediately recentrifuged for 2 hr at 43K and 4° C. The pellet was then resuspended in 10 mL of pH 7.0, 0.1M $PO_4$ buffer and recentrifuged at 43K, °C. for 2 hr. This pelleted pellet was resuspended in 7.5 mL of $H_2O$. After ageing overnight at 4° C. the suspension was centrifuged at 1000 rpm for 3 min and the supernatant removed as the final conjugate.

Assays: Lowry Protein: 0.920 mg/mL; Phenol sulfuric acid assay: 0.212 mg/mL; Ps/Pro=0.23; SCMHC/lys=0.031; SCMC/lys=0.022.

Upon administration of this conjugate to mice or African Green Monkeys, high titers of anti-Pn4-Ps antibodies were raised as measured by Pn4-Ps specific ELISA assay.

EXAMPLE 28

Preparation of the Pn9V-Ps Intermediate:

(1) Sonic Hydrolysis: A 1.0-g portion of Pn 9V Ps powder was solubilized in 400 mL saline (0.9% NaCl) with stirring at room temperature for about 4 hours. The solution was then sonicated in a plastic beaker in an ice bath with a Branson Sonifier (one-half inch probe, setting 8) for an interval of 3 minutes. The viscosity was checked after this interval. After 13 min., another 1 min. sonication was performed to obtain a viscosity endpoint of 1.117 centistokes was obtained. The hydrolyzed sample was brought to room temperature and sodium acetate reagent (19.5 g) was added to a final concentration of 3% (w/v).

(2) Serological Probe: An isopropanol (IPA) fractionation pilot study and antibody-directed end-point Nephelose assay, performed on a 10 mL portion of the sample, showed that the Pn 9V Ps would precipitate between 40–45% IPA.

(3) First IPA Addition: The hydrolyzed sample [volume=391 mL, from step 1 above] was brought to 41.8% IPA by the addition of 281 mL IPA (added dropwise with stirring at room temperature). The sample was allowed to stir for 15–30 minutes and then centrifuged at 11,000×g for 30 minutes (Beckman JA-10 rotor; 8,000 rpm; 20° C.). The waste pellet was triturated with absolute EtOH in a 250-mL Omnimix jar, then collected on a 60-mL sinter glass funnel. The precipitate was washed directly on the funnel with absolute EtOH, then acetone, and dried in vacuo over $CaCl_2$ at room temperature in preparation for analysis.

(4) Second IPA Addition and Product Recovery: The 41.8% IPA supernatant fluid [volume=637 mL, from step 3 above] was brought to 44.3% IPA by adding 28.6 mL IPA dropwise while stirring at room temperature. The sample was aged and centrifuged as in step 3 above. The pellet was triturated, collected, washed and dried as in step 3 above. The Pn9V-Ps product weighed 342.2 mg.

(5) Dialysis and Lyophilization: A portion (347 mg) of the Pn-Ps sample from Step 4 above was solubilized in 139 mL of distilled $H_2O$ at room temperature for 4–5 hours. The solution (2.5 mg/mL) was transferred to dialysis tubing (12,000 MW cutoff; 45 mm) and dialyzed vs. distilled $H_2O$ at 4° C. for 25 hours with 2 additional changes of distilled $H_2O$. Then the sample was transferred to lyophilization flasks, shell frozen in a dry ice:methanol bath and lyophilized on a Virtis (Freezemobile) lyophilizer for 2–3 days. The recovery of the final Ps product was 303.5 mg. The final product had a $K_d$=0.60.

(6) Third IPA Addition and Product Recovery: The 44.3% IPA supernatant fluid [volume=655 mL, from step 4 above] was brought to 46.8% IPA by adding 30.8 mL IPA dropwise while stirring at room temperature. The sample was aged and centrifuged as in step 3 above. The pellet was triturated, collected, washed and dried as in step 3 above. The Pn9V-Ps product weighed 410.8 mg.

(7) Dialysis and Lyophilization: A portion (420.4 mg) of the Pn-Ps sample from Step 6 above was solubilized in 168 mL of distilled $H_2O$ at room temperature for 4–5 hours. The solution (2.5 mg/mL) was transferred to dialysis tubing (12,000 MW cutoff; 45 mm) and dialyzed vs. distilled $H_2O$ at 4° C. for 25 hours with 2 additional changes of distilled $H_2O$. Then the sample was transferred to lyophilization flasks, shell frozen in a dry ice:methanol bath and lyophilized on a Virtis (Freezemobile) lyophilizer for 2–3 days. The recovery of the final Ps product was 342.5 mg. The final product had a $K_d$=0.65.

(8) It is obvious to those skilled in the art that the products in steps 4 & 6 could have been collected together with a larger addition of IPA, then dialyzed and lyophilized as a single product with analytical characteristics of the weighted average of the characteristics of the individual subfractions. It should alos be obvious to those skilled in the art that Pn1-Ps or Pn5-Ps could be treated in the same way as Pn9V-Ps or Pn4-Ps as disclosed herein.

EXAMPLE 29

Conjugation of Pn9V-Ps with OMPC:

Pn9V-Ps prepared according to Example 28, is conjugated in the same manner as Pn4-Ps as shown in Example 27.

EXAMPLE 30

Quantitative Determination of Acetate in Pn9V/18C-Ps and Pyruvate in Pn4-Ps:

A method was developed to quantify the retention of O-pyruvate in Pn4-Ps and O-acetate groups in Pn9V-Ps and Pn18C-Ps during processing of pneumococcal (Pn) capsular polysaccharides (Ps). The O-acetyl or O-pyruvate groups are first released by hydrolysis, then the acetate and pyruvate in the PnPs hydrolysate are identified and quantitated using high performance anion-exchange chromatography coupled with suppressed conductivity.

Samples of unprocessed and processed Pn4, Pn9V, and Pn18C were analyzed by this method. The preliminary results showed an approximate 1:1 and 0.8:1 molar ratio of pyruvate to each Ps repeating unit for unprocessed and sized Pn4, respectively. The molar ratios of acetate to each Ps repeating unit in Pn18C-Ps were found to be 1:1 and 0.8:1 for unprocessed and sized samples, respectively; 1.7:1 and 1.5:1 for unprocessed and sized Pn9V, respectively. A sample of Pn18C-Ps-OMPC conjugate aqueous bulk was also analyzed for the molar ratio of O-acetate to each Ps repeating unit and found to be approximately 0.5:1.

It has been reported in the literature that the pyruvate group is a powerful immunodeterminant in type 4 capsular polysaccharides, and its removal gives rise to marked changes in immunological specificity [Heidelberger, M., Dudman, W. F., and Nimmich, W., 'Immunochemical relationships of certain capsular polysaccharides of Klebsiella, pneumococci, and Rhizobia.' *J. Immunol.*, 104:1321–1328, (1970); Higginbotham, J. D., Heidelberger, M., and Gotschlich, E., 'Degradation of a pneumococcal type-specific polysaccharide with exposure of group-specificity.' *Proc. Natl. Acad. Sci. USA* 67:138–142, (1970)]. Similarly, the removal of the O-acetate group in type Pn1SC-Ps polysaccharide abolished its immunological specificity. [Estrada-Parra, S., and Heidelberger, M., 'The specific polysaccharide of type XVIII pneumococcus.' *Biochemistry*, 2:1288–1294, (1963)]. It was therefore essential to develop a quantitative method for the determination of acetate and pyruvate in Pn18C-Ps, and Pn4. O-acetyl groups in Pn9V may also play an important role in the immunological structure of Pn9V since the de-O-acetylated Pn9V had no antigenic reactivity as determined by rate nephelometric measurement.

We found that O-acetate is easily released from Pn9V and Pn1SC-Ps at alkaline conditions (pH 11) at 4° C. and O-pyruvate is easily released from Pn4 upon heating at 65° C. We found that acetate and pyruvate can be separated from a hydrolyzed PnPs sample using an OmniPac PAX500 column at the flow rate of 1 ml/min with 0.98 mM NaOH and 2% MeOH as the mobile phase. The detection was accomplished by suppressed conductivity detection using 25 mM $H_2SO_4$ as the regenerant at a flow rate of 10 ml/min. Optimal hydrolysis conditions for quantitative HPLC analysis of O-acetate and O-pyruvate from Pn18C-Ps, 9V and Pn4, respectively are disclosed in this example.

Instrumentation

A Dionex BioLC was equipped with an OmniPac PAX-500 guard, and analytical column (4.6×250 mm). Suppressed conductivity detection was accomplished using 25 mN sulfuric acid as the regenerant. The flow rate was set at 10 ml/min with a Dionex autoregen unit. The mobile phase and gradient program for separating acetate and pyruvate from a sample of hydrolyzed PnPs are listed in the following table:

Buffer 1—1 mM sodium hydroxide
Buffer 2—100% methanal
Buffer 3—200 mM sodium hydroxide
Buffer 4—water

| Time | % Buffer 1 | % Buffer 2 | % Buffer 3 | % Buffer 4 | Flow (ml/min) |
|---|---|---|---|---|---|
| 0 | 98 | 2 | 0 | 0 | 1 |
| 12.5 | 98 | 2 | 0 | 0 | 1 |
| 12.6 | 58 | 2 | 0 | 40 | 1.5 |
| 20.0 | 58 | 2 | 0 | 40 | 1.5 |
| 20.1 | 98 | 2 | 0 | 0 | 1.5 |
| 30.0 | 98 | 2 | 0 | 0 | 1.5 |
| 30.1 | 98 | 2 | 0 | 0 | 1 |
| 50.0 | 98 | 2 | 0 | 0 | 1 |

Using these conditions and a detector sensitivity of 3 μSiemens, 4 nanomoles each of acetate and pyruvate which elute at retention times of approximately 5.2 and 9.5 minutes, respectively can be easily detected.

Sample Preparation

Purified PnPs samples from Merck Manufacturing Division were subjected to Karl-Fisher titration using an Aquastar V3000 volumetric moisture titrator to determine the content of residual $H_2O$, and then dissolved in Milli-Q $H_2O$ at a concentration of 1.0 mg dry weight per ml. Samples (100 μg/ml) were treated in 2 mM NaOH for 16 h at room temperature to remove O-acetate from Pn9V-Ps and Pn18C-Ps samples. Pn4-Ps samples were hydrolyzed in 1 mM HCl at 65° C. for 16 h for the removal of O-pyruvate from Pn4. Samples of sized Pn9V and Pn18C-Ps and Pn18C-Ps-OMPC conjugate aqueous bulk were also subjected to monosaccharide compositional analyses by high-pH anion-exchange chromatography and pulsed amperometric detection. The monosaccharide compositional analysis was performed to obtain the correct concentration of PnPs in the sized and aqueous conjugate bulk samples.

Acetate, pyruvate and N-Acetylmannosamine standards were dissolved in Milli-Q $H_2O$ at the concentration of 200 nmole/ml.

Hydrolysis of Samples and Standards

De-O-acetylaction of Pn18C-Ps was investigated by treating Pn18C-Ps, at four NaOH concentrations (1, 2, 5, and 50 mM) at various temperatures (4°, 25°, 45°, and 65° C.) and various times (3, 5, and 16 hours). Standard solutions of acetate, pyruvate and N-Acetylmannosamine were also included in the study to determine if the conditions necessary for de-O-acetylation would also result in degradation of acetate/pyruvate or the loss of N-acetyl groups.

The removal of pyruvate from Pn4 was studied following treatment with either sodium hydroxide (50 mM/100° C./16 hr) or hydrochloric acid at various concentration (1, 10, 100 mM), times (3, 5, and 16 hours), and temperatures (65°, 85°, and 100° C.)

Rate Nephelometry

The rate nephelometric activity of Pn9V-Ps, Pn18C-Ps and Pn4-Ps before and after de-O-acetylation or de-O-pyruvylation was measured. Samples were diluted to 1, 1.5, 2, and 2.5 μg/ml.

High Performance Size Exclusion Chromatography (HPSEC)

The HPSEC of Pn9V-Ps, Pn18C-Ps and Pn4 before and after de-O-acetylation or de-O-pyruvylation was measured. A 7.5×600 mm TSK G6000PW column equipped with a flow restrictor was heated to 50° C. at 800–1000 psi and equilibrated with 0.2M sodium acetate at 0.3 ml/min. A 60 μg sample (1 mg/ml) was injected on the column and eluted with the mobile phase at 0.3 ml/min. The column eluant was mixed with post column addition of 0.5M NaOH at a flow rate of 0.5 ml/min and monitored with a Dionex pulsed amperometric detector, and the Kd measured.

Assay Sensitivity and Linearity

Detector linearity and sensitivity were determined at 3 μSiemens for both pyruvate and acetate. Pyruvate and acetate were detectable at a lower limit of 0.125 nanomoles. Detector response for both components was linear through 2 nanomoles with correlation coefficients of 0.9999 and 0.9992 for pyruvate and acetate, respectively.

Omtimization of O-acetate Removal from Pn18C-Ps

Preliminary studies of the time course hydrolysis Pn18C-Ps demonstrated the lability of O-acetyl group to alkaline hydrolysis at low temperatures. 2 mM sodium hydroxide was sufficient to completely de-O-acetylate Pn1SC-Ps at 4° C. after a 16 hour incubation. Higher temperatures (>25° C.) treatments were found to release N-acetate from N-acetylmannosamine which would interfere the measurement of Pn9V O-acetate. The optimal hydrolysis condition for the removal of O-acetate from PnPs was found to be 16 h at 4° C. Less then 1% of acetate was found to be removed from a standard of N-acetylmannosamine treated with 2 mM NaOH for 16 h at room temperature.

Optimization of O-pyruvate Removal from Pn4

Hydrolysis studies of Pn4 initially were undertaken using sodium hydroxide hydrolysis. It was quickly discovered that very little pyruvate was recovered when sodium hydroxide was used. Initial control studies demonstrated that pyruvate was cleaved from Pn4 in $H_2O$ at 100° C. With this information, it was decided to carry out the optimization studies for O-pyruvate release from Pn4 using HCl hydrolysis at elevated temperatures. Some degradation of the pyruvate appeared at higher temperatures. This can be demonstrated with a sample of pyruvate standard which has been hydrolyzed under the same conditions as Pn4. Maximum recovery of pyruvate occurred when hydrolysis was carried out in 1 mM HCl for 16 hours 65° C.

Analysis of O-acetate and O-pyruvate in PnPs Samples

Various samples representing starting PnPs, sized PnPs and one Pn18C-Ps-OMPC conjugate were analyzed for O-acetate/pyruvate by the HPLC method described above after hydrolysis in 2 mM NaOH at room temperature to release O-acetate in Pn9V-Ps/18C or in 1 mM HCL at 65° C. for release O-pyruvate in Pn4-Ps. The results of this study are presented below:

| Sample | Ratio of pyruvate/acetate to each Ps repeating unit |
| --- | --- |
| Pn4, sample 1 | 1.0 |
| Pn4, sample 2 | 0.8 |
| Pn9V, sample 1 | 1.7 |
| Pn9V, sample 2 | 1.5 |
| Pn18C-Ps, sample 1 | 1.0 |
| Pn18C-Ps, sample 2 | 0.8 |
| Pn18C-Ps-OMPC aqueous bulk | 0.5 |

The results show that the retension of the side groups in the sized PnPs were approximately 90% for Pn9V-Ps and 80% for Pn4 and 18C. The retention of O-acetate in Pn1SC-Ps-OMPC conjugate aqueous bulk was found to be approximately 50%. The theoretical values for Pn18C-Ps and Pn4 are 1 mole of acetate or pyruvate per mole of Ps repeating unit and for Pn9V the ratio is 2:1. [Jansson, P-E., Lindberg, B., and Lindquist, U. 'Structural studies of the capsular polysaccharides from Streptococcus pneumoniae Type 4.' *Carbohyd. Res.*, 95:73–80, (1981). Lugrowski, C. and Jennings, H. J. 'Structural determination of the capsular polysaccharide of *Streptococcus pneumoniae* Type 18C.' *Carbohyd. Res.* 131:119–129, (1984). Perry, M. B., Daoust, V., and Carlos, D. J. 'The specific capsular polysaccharide of *Streptococcus pneumoniae* Type 9V.' *Can. J. Biochem.* 59:524–533, (1981)]. The lower retention of O-acetate found in the Pn1SC-Ps-OMPC conjugate is expected due to the susceptibility of O-acetyl groups hydrolysis to alkaline conditions at low temperatures.

The rate nephelometric activity of samples of Pn4, Pn9V, and Pn18C-Ps and de-O-pyruvylated and de-O-acetylated samples were measured. The results shown that the nephelose activity was lost completely after removal of these side groups, even though the Kd of the untreated samples. The Kd's were obtained by the HPSEC method described above. However, the Kd of Pn4 after de-O-pyruvylation by mild acid hydrolysis was increased from 0.60 to 0.68 and the appearance near the salt volume. The antigenicity date for Pn4 and Pn18C-Ps support the work of other investigators regarding the importance of these side groups in pneumococcal polysaccharide immunologic reactivity. The results for Pn9V suggest that in addition to glucuronic acid, the O-acetyl groups of this molecule are important immunologic determinants as well.

Thus, according to this method, a rapid, sensitive procedure for the quantitative analysis of O-pyruvyl ketal in Pn4 and O-acetate in Pn9V and Pn18C-Ps has been developed. This procedure is valuable in defining the correct process for sizing and conjugation of Pn4, Pn9V, and Pn18C-Ps in order to retain the antigenic structure of these polysaccharides.

EXAMPLE 31

Isolation of Pn6B-Ps-MIEP Conjugate:

1. Two conjugate reaction mixture samples (one representing a $H_2O$ dialyzed sample of the other) were stored at 3–8 C until used.

2. 0.2 MOPS pH 7.2 buffer was added to the samples to obtain a final concentration of about 7 mM. Solid GuHCl was added to the sample to achieve a final concentration of 4.2M (Note: 1.42 g of GuHCl/ml of sample should be added to compensate the increase in volume due to the addition of the solid GuHCl. Likewise, buffer addition should be adjusted to account for the volume increase so that the sample composition is closer to the column eluent composition. Alternatively, the sample could be dialysed against the column eluent prior to the chromatography).

3. 2.8 ml of sample (containing about 1 mg of protein based on lowry protein assay) were injected onto 12.6×96 cm column of sephacryl S-1000 equilibrated in 10 mM MOPS pH 7.2, 6 m GuHCl at a flow rate of 0.6 ml/min. Column effluent was continuously monitored at 280 nM (perkin Elmer LC 235 diode array detector) and 3 ml fractions were collected.

4. Protein distribution was based on A280 (as well as spectra) and Pn6B-Ps distribution was based on a Pn6B-Ps specific ria assay. Based on elution positions of Pn6B-Ps-BrAc alone and in physical mixtures with unactivated MIEP, pools of fractions containing both PS and protein were made and those eluting distinctly from the positions observed for the Pn6B-Ps-BrAc were presumptively designated as Pn6B-Ps-MIEP conjugate.

5. Pools were concentrated by ultrafiltration using a YM-30 membrane and diafiltered using Milli-Q H$_2$O. Protein and Pn6B-Ps content were estimated from quantitive compositional studies. The presence of SCMHC was detected by amino acid analysis.

EXAMPLE 32

Pneumococcal Polysaccharide Pn18C-Ps Direct RIA Assay

This assay is used for the quantitation of pneumococcal polysaccharide type 18C. It is a multilayer sandwich RIA assay. Rabbit anti-Pn18C-Ps is coated on polystyrene beads. The beads are incubated in a sample solution containing Pn18C-Ps. After incubation, the beads are washed and reincubated in a second solution containing a mouse antibody to Pn18C-OMPC. After this incubation the beads are washed and incubated a third time in a solution containing $^{125}$I-goat anti-mouse IgG. The plates are once again washed, after which the beads are transferred to plastic tubes for counting. Unknown samples of Pn18C-Ps are compared to a standard curve for quantitation.

Equipment

1. RIA kit: Abbot Labs, Diagnostic Div., Catalog No. 6171-10.
2. Qwik Wash System, Abbot Labs, Diagnostic Div.
3. Adjustable pipettes and disposable pipette tips (ex. Eppendorf digital)
4. Gamma Counter (ex. Abbott Autologic).
5. ¼" polystyrene beads with specular finish: Precision Plastic Ball Co., 3000 N. Cicero Ave., Chicago, Ill. 60641.

Reagents

1. New York State Health Services Anti-Pn1SC-Ps antibody lot R18-44 or equivalent.
2. Mouse anti-Pn1SC-Ps OMPC antisera (pool 11260-235 or equivalent).
3. Goat, anti-mouse IgG $^{125}$I-labeled antisera: NEX 159, New England Nuclear, 549 Albany Street, Boston, Mass. 02118.
4. Incubation Buffer: RCM8 containing 1.0% BSA Sigma A2153 0.1% azide Sigma S2002

5. Diluent

| | |
|---|---|
| 8 parts fetal calf serum | Sigma F3885 |
| 1 part goat serum | Sigma G6767 |
| 1 part rabbit serum | Sigma R4505 |
| 0.05% TWEEN 20 | Sigma P1379 |
| 0.1% azide | Sigma S2002 |

3. Add 1 anti-Pn1SC-Ps coated bead to each well of the plate containing a sample or standard and agitate the plate gently to insure that all beads are completely covered with buffer.
4. Cover the plate with an adhesive backing provided with the RIA kit and incubate the plate at room temperature for 6 hours.
5. Wash the plate using the Qwik Wash apparatus and deionized water.
6. Dilute the mouse anti-18C antibody 1:1000 in diluent.
7. Add 200 µl of this solution to each well containing a bead.
8. Cover the plate and incubate overnight at room temperature.
9. Wash the plate using the Qwik Wash apparatus and deionized water.
10. Dilute $^{125}$I-labeled goat, anti-mouse antibody to 15000 cpm/10 µl in diluent (~1:160 dilution).
11. Add 20 µl of this solution to each well containing a bead.
12. Cover the plate and incubate at 37° C. for 2 hours.
13. Wash the plate using the Qwik Wash apparatus and deionized water.
14. Transfer the beads to the plastic tubes provided with the RIA kit and count using a suitable gamma counter.

Calculations

1. Combine the duplicate measurements together to get an average for each sample, standard, and Incubation Buffer control. Substract the Incubation Buffer control from all standards and samples.

Using a calculator equipped for statistical calculations, input the data for the standard curve and calculate the correlation coefficient and slope of the line.

Using the appropriate standard curve (free for free, conjugate for conjugate), calculate the response of the samples, and correct for dilutions.

The same procedure described above is applicable to any of the other Pn-Ps species by substituting type specific reagents.

What is claimed is:

1. A conjugate comprising an immunogenic protein selected from OMPC and MIEP covalently linked to a polysaccharide derived from one or more subtypes of *Streptococcus pneumoniae*, said polysaccharide having, on average, between 60 and 1200 repeating units per molecule and a polydispersity between 1.0 and 1.4, wherein said polysaccharide has a molecular weight between, on average, $1 \times 10^5$ and $1 \times 10^6$, and a level of contamination by pneumococcal group-specific C-polysaccharide below 3.0% of the type-specific polysaccharide.

2. The conjugate of claim 1 wherein said polysaccharide has an antigenicity index between 0.4 and 1.1.

3. The conjugate of claim 2 wherein said polysaccharide has an intrinsic viscosity between 0.6 and 3.0 dL/g and an antigenicity index of between 0.7 and 1.1.

4. The conjugate of claim 3 wherein said polysaccharide is derived from any of the subtypes of *Streptococcus pneumoniae* selected from: 1, 2, 3, 4, 5, 6B, 7F, 8, 9N, 9V, 10A, 11A, 12F, 14, 15B, 17F, 18C, 19F, 19A, 20, 22F, 23F, and 33F.

5. The conjugate of claim 4 wherein said polysaccharide is derived from between one and all of the capsular polysaccharides from *Streptococcus pneumoniae* subtype: 4, 6B, 9V, 14, 18C, 19F, or 23F.

6. The conjugate of claim 5 wherein said polysaccharide has a size polydispersity between 1.0 and 1.4, more than 60 repeating units per molecule, a C-polysaccharide contamination level as compared with type specific polysaccharide of less than 3%, and is derived from:

1) *Streptococcus pneumonias* 6B, said polysaccharide having:
  a) a $M_N$ between about $3 \times 10^5$ and $6 \times 10^5$;
  b) a $K_d$ (peak) of about $0.60 \pm 0.05$;
  c) a $M_W$ between about $3 \times 10^5$ and $7 \times 10^5$;
  d) an intrinsic viscosity in 0.1M sodium phosphate, pH 7.2, between 1.0 and 2.0; and
  e) less than about 1000 repeating units per molecule on average;

2) *Streptococcus pneumoniae* 14, said polysaccharide having:
  a) a $M_N$ between about $3 \times 10^5$ and $8 \times 10^5$;
  b) a $K_d$ (peak) of about $0.60 \pm 0.05$;
  c) a $M_W$ between about $4 \times 10^5$ and $1 \times 10^6$; and
  d) an intrinsic viscosity in 0.1M sodium phosphate, pH 7.2, between 0.6 and 1.6; and
  e) less than about 1200 repeating units per molecule on average;

3) *Streptococcus pneumoniae* 19F, said polysaccharide having:
  a) a $M_N$ between about $2 \times 10^5$ and $6 \times 10^5$;
  b) a $K_d$ (peak) of about $0.65 \pm 0.05$;
  c) a $M_W$ between about $2 \times 10^5$ and $6 \times 10^5$;
  d) an intrinsic viscosity in 0.1M sodium phosphate, pH 7.2, between 1.0 and 2.0; and
  e) less than about 1000 monomer repeating units per molecule, on average;

4) *Streptococcus pneumonias* 23F, said polysaccharide having:
  a) a $M_N$ between about $2 \times 10^5$ and $6 \times 10^5$;
  b) a $K_d$ (peak) of about $0.54 \pm 0.05$;
  c) a $M_W$ between about $4 \times 10^5$ and $8 \times 10^5$;
  d) an intrinsic viscosity in 0.1M sodium phosphate, pH 7.2, between 1.5 and 3.0; and
  e) less than about 1000 monomer repeating units per molecule, on average;

5) *Streptococcus pneumoniae* 4, said polysaccharide having:
  a) a $M_N$ between about $2 \times 10^5$ and $4 \times 10^5$;
  b) a $K_d$ (peak) of about $0.65 \pm 0.05$;
  c) a $M_W$ between about $2 \times 10^5$ and $5 \times 10^5$;
  d) an intrinsic viscosity in 0.1M sodium phosphate, pH 7.2, between 1.0 and 3.0; and
  e) less than about 600 monomer repeating units per molecule, on average;

6) *Streptococcus pneumonias* 9V, said polysaccharide having:
  a) a $M_N$ between about $3 \times 10^5$ and $6 \times 10^5$;
  b) a $K_d$ (peak) of about $0.65 \pm 0.05$;
  c) a $M_W$ between about $3 \times 10^5$ and $7 \times 10^5$;
  d) an intrinsic viscosity in 0.1M sodium phosphate, pH 7.2, between 1.0 and 2.0; and
  e) less than about 800 monomer repeating units per molecule, on average; or 7) *Streptococcus pneumonias* 18C, said polysaccharide having:
  a) a $M_N$ between about $2 \times 10^5$ and $6 \times 10^5$;
  b) a $K_d$ (peak) of about $0.65 \pm 0.05$;
  c) a $M_W$ between about $2 \times 10^5$ and $6 \times 10^5$;
  d) an intrinsic viscosity in 0.1M sodium phosphate, pH 7.2, between 1.5 and 3.0. and e) less than about 700 monomer repeating units per molecule, on average; or a mixture of any of these polysaccharides.

7. The covalent conjugate of claim 6 wherein the OMPC or MIEP and the Pn-Ps are linked through a spacer as shown by the formula:

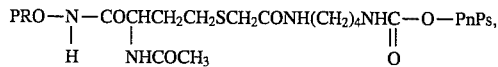

for linkagages through the polysaccharide hydroxyls, or

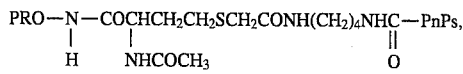

in the case of polysaccharides bearing unblocked carboxyllic acid groups, wherein PRO represents OMPC or MIEP, and Pn-Ps represents a penumococcal polysaccharide.

8. The conjugate of claim 7 wherein the conjugate has a Pn-Ps:OMPC, or Pn-Ps:MIEP mass ratio between about 0.05 and 0.5, and upon hydrolysis and amino acid analysis yields a SCMHC/Lys ratio between 0.01 and 0.15.

9. A pneumococcal polysaccharide-immunogenic protein conjugate produced by the process of:

(a) Culturing a pneumococcus and isolating crude pneumococcal polysaccharide or solubilizing pneumococcal polysaccharide powder;

(b) Purifying and partially-hydrolyzing the polysaccharide of step (a) to an endpoint predetermined to generate a polysaccharide amenable to conjugation having no more than a 30% reduction of the polysaccharide's type-specific antigenicity as compared with the crude polysaccharide of step (a); and (c) Conjugating the product of step (b) with OMPC or MIEP; wherein the pneumococcus cultured in step (a) is selected from one or more of the subtypes: 4, 6B, 9V, 14, 18C, 19F, 23F, 1, 5, 7F, and further, wherein the Pn-Ps retains its antigenic integrity as measured by Ouchterlony double immunodiffusion or rate nephelometry assay using an anti-Pn-Ps type-specific antibody, said Pn-Ps prior to conjugation being physically sheared in a Gaulin press at a pressure between about 2000 and 15000 PSI or hydrolyzed by heating at 100° C. for 24 hours or by sonicating, to a viscosity for a 1 mg/ml solution in 0.9M sodium chloride or $K_d$ (peak) endpoint as follows for each listed Pn-Ps subtype:

| Pn-Ps Subtype | Target Endpoint Viscosity (centistokes) | Target Endpoint $K_d$ (peak) |
|---|---|---|
| Pn4-Ps | 1.5–1.00 | 0.65 ± 0.05 |
| Pn6B-Ps | 1.3–1.00 | 0.60 ± 0.05 |
| Pn6B-Ps | 1.3–1.00 | 0.60 ± 0.05 |
| Pn9V-Ps | 1.3–1.00 | 0.65 ± 0.05 |
| Pn14-Ps | 1.1–0.95 | 0.60 ± 0.05 |
| Pn18C-Ps | 1.5–1.00 | 0.65 ± 0.05 |
| Pn19F-Ps | 1.3–1.00 | 0.65 ± 0.05 |
| Pn23F-Ps | 1.5–1.00 | 0.54 ± 0.05; | optionally followed by chromatographic or alcohol fractionation to select material having a polydispersity below 1.4.

10. A process for making a Pn-Ps-PRO conjugate which comprises:

a) Isolating crude pneumococcal polysaccharide, Pn-Ps;

b) i-Optionally purifying the crude Pn-Ps by ion exchange adsorption of impurities; ii-Partially-hydrolyzing or mechanically-shearing the crude Pn-Ps;

Fractionating the partially-hydrolyzed Pn-Ps according to size and purity;

d) Derivatizing the fractionated Pn-Ps, derived from one or more pneumococcal subtypes according to steps (a)–(c), to display pendant nucleophilic or electrophilic moieties;

e) Isolating Neisseria meningitidis b OMPC, or MIEP;

f) Functionalizing the OMPC or MIEP to exhibit reactive electrophilic or nucleophilic moieties;

g) Conjugating the polysaccharide of step (d) with the protein of step (f);

h) Capping the conjugate to remove residual functional groups; and i) Isolating the conjugate product, wherein steps (b) and (c) further comprise:

(b) 1-Optionally, adsorbing onto Whatman DE52 anionic impurities at a solution pH of about 5; 2-Partially hydrolyzing the Pn-Ps in solution to an endpoint viscosity predetermined to diminish the Pn-Ps binding to anti-pneumococcal type specific antibody by no more than 30% as compared with crude Pn-Ps by:

1. heating at 50° to 150° C. for between 1 to 48 hours; or 2. sonicating for periods of 5 seconds to 5 minutes, depending on the power setting of the sonication probe, followed by periods of cooling and additional sonication; or 3. shearing in a Gaulin press at pressures between about 2000 and 15000 PSI; and c) Fractionating the partially-hydrolyzed Pn-Ps according to size and purity wherein step (c) comprises:

Fractionating the hydrolyzed Pn-Ps and selecting a fraction having a molecular weight in the range between $1 \times 10^5$ and $1 \times 10^6$ by:

i-differential alcohol solubility using isopropanol at concentrations predetermined to precipitate the desired Pn-Ps size range, or ii-fractionation on a size-exclusion liquid chromatography column capable of including and fractionating polysaccharides in the size range between $5 \times 10^4$ and $1 \times 10^6$ wherein the endpoint for hydrolysis or shear is determined by viscometry of a 1 mg/ml solution in 0.1M sodium phosphate, pH 7.2, or chromatography for each of the listed polysaccharides according to the end-point for that subtype Pn-Ps:

| Pn-Ps Subtype | Target Endpoint Viscosity (centistokes) | Target Endpoint $K_d$ (peak) |
|---|---|---|
| Pn4-Ps | 1.5–1.00 | 0.65 ± 0.05 |
| Pn6B-Ps | 1.3–1.00 | 0.60 ± 0.05 |
| Pn9V-Ps | 1.3–1.00 | 0.65 ± 0.05 |
| Pn14-Ps | 1.1–0.95 | 0.60 ± 0.05 |
| Pn18C-Ps | 1.5–1.00 | 0.65 ± 0.05 |
| Pn19F-Ps | 1.3–1.00 | 0.65 ± 0.05 |
| Pn23F-Ps | 1.5–1.00 | 0.54 ± 0.05. |

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

ACTAGTTGAA ATGAAAAAAT CCCTG 25

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

GAATTCAGAT TAGGAATTTG TT 22

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:3:

AGCTCGGATC CG 12

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

AAGCTCGGAT CCTAGTTGCA ATG 23

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:5:

CTAAGCTTAA CAAAATGGAC GTTACCTTGT ACGGTACAAT T 41

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

```
ACGGTACCGA  AGCCGCCTTT  CAAG                                    24
```